United States Patent
Boyden et al.

(10) Patent No.: US 11,346,842 B2
(45) Date of Patent: May 31, 2022

(54) SINGLE MOLECULE PEPTIDE SEQUENCING METHODS

(71) Applicant: Massachusetts Institute of Technology, Cambridge, MA (US)

(72) Inventors: Edward Boyden, Cambridge, MA (US); Adam Henry Marblestone, Cambridge, MA (US); Samuel Gordon Rodriques, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 54 days.

(21) Appl. No.: 16/907,831

(22) Filed: Jun. 22, 2020

(65) Prior Publication Data

US 2020/0400677 A1 Dec. 24, 2020

Related U.S. Application Data

(60) Provisional application No. 62/864,051, filed on Jun. 20, 2019.

(51) Int. Cl.
*G01N 33/68* (2006.01)
*C12Q 1/37* (2006.01)
*G01N 21/64* (2006.01)
*G01N 21/76* (2006.01)

(52) U.S. Cl.
CPC ............ *G01N 33/6824* (2013.01); *C12Q 1/37* (2013.01); *G01N 21/6428* (2013.01); *G01N 21/6458* (2013.01); *G01N 21/76* (2013.01); *G01N 2333/948* (2013.01)

(58) Field of Classification Search
CPC .......... G01N 33/6824; G01N 21/6428; G01N 21/6458; G01N 21/76; G01N 2333/948; G01N 21/648; G01N 2021/6439; C12Q 1/37
See application file for complete search history.

(56) References Cited

U.S. PATENT DOCUMENTS

| 9,435,810 | B2 | 9/2016 | Havranek et al. |
| 9,625,469 | B2 | 4/2017 | Marcotte |
| 2014/0273004 | A1* | 9/2014 | Havranek ...... C12Y 304/11018 435/7.1 |

FOREIGN PATENT DOCUMENTS

WO 2010065531 A1 1/2010

OTHER PUBLICATIONS

Bellin, DL, et al., "Interfacing CMOS Electronics to Biological Systems: from Single Molecules to Cellular Communities Biomedical Circuits and Systems Conference." (BioCAS), 2014 IEEE. IEEE; 2014. p. 476-479.
Bentley, et al., "Accurate whole human genome sequencing using reversible terminator chemistry." Nature. vol. 456, Nov. 6, 2008, p. 53-59.

(Continued)

*Primary Examiner* — Jennifer Wecker
*Assistant Examiner* — Michael Paul Shimek
(74) *Attorney, Agent, or Firm* — Pierce Atwood LLP

(57) ABSTRACT

The invention, in part, includes methods of single molecule protein sequencing that include using weak binding spectra in the amino acid identification.

20 Claims, 11 Drawing Sheets
(11 of 11 Drawing Sheet(s) Filed in Color)

(56) References Cited

OTHER PUBLICATIONS

Borgo, B. "Strategies for Computational Protein Design with Application to the Development of a Biomolecular Tool-kit for Single Molecule Protein Sequencing." Theses and Dissertations (ETDs) at//openscholarship.wustl.edu/etd/1221. May 2014. 203 pages.
Borgo, B., et al., "Motif-directed redesign of enzyme specificity." Protein Science. 2014; vol. 23, p. 312-320.
Borgo, et al., "Computer-aided design of a catalyst for Edman degradation utilizing substrate-assisted catalysis." Protein Science, Dec. 16, 2014 doi: 10.1002/pro.2633, vol. 24, p. 571-579.
Brenner, et al., "Gene expression analysis by massively parallel signature sequencing (MPSS) on microbead arrays." Nature Biotechnology vol. 18, p. 630-634 (2000).
Chandradoss SD et al., "Surface Passivation for Single-molecule Protein Studies." Journal of Visualized Experiments: JoVE. Apr. 2014; (86), 8 pgs.
Cui Y, et al., "Nanowire Nanosensors for Highly Sensitive and Selective Detection of Biological and Chemical Species." Science. 2001;293(5533): 1289-1292.
Dempsey, GT, et al., "Evaluation of fluorophores for optimal performance in localization-based super-resolution imaging." Nature Methods. 2011;8(12): 1027-1036.
Edman, P. "Method for Determination of the Amino Acid Sequence in Peptides." Acta Chem Scand. (1950) 4(7):283-293.
Finkelstein, et al., "Supported Lipid Bilayers and DNA Curtains for High-Throughput Single-Molecule Studies." Methods Mol Biol. 2011 ; 745: 447-461.
Foote, J. et al., "Kinetic and affinity limits on antibodies produced during immune responses." PNAS (USA) vol. 92, pp. 1254-1256, Feb. 1995.
Groll, J., et al., "Chapter 1—Star Polymer Surface Passivation for Single-Molecule Detection." Methods in Enzymology. vol. 472. Elsevier; 2010. p. 1-18.
Guo, N, et al., "CMOS Time-Resolved, Contact, and Multispectral Fluorescence Imaging for DNA Molecular Diagnostics." Sensors. 2014; 14(11):20602-20619.
Joo C., et al,. "Bringing single-molecule spectroscopy to macromolecular protein complexes." Trends Biochem Sci. Jan. 2013; 38(1): 30-37.
Joo et al., "Single-Molecule FRET with Total Internal Reflection Microscopy." Health Sciences (2012) 1223-1237.
Jungmann, R, et al., "Single-Molecule Kinetics and Super-Resolution Microscopy by Fluorescence Imaging of Transient Binding on DNA Origami." Nano letters. 2010; 10(11):4756-4761.
Kim, A, et al., "Ultrasensitive, label-free, and real-time immunodetection using silicon field-effect transistors." Applied Physics Letters 91, 103901 (2007).
Laursen, R. A. "Solid-Phase Edman Degradation—An Automatic Peptide Sequencer." Eur. J. Biochem. 20 (1971) 89-102.
Lu, N. et al., "Label-Free and Rapid Electrical Detection of hTSH with CMOS-Compatible Silicon Nanowire Transistor Arrays." ACS Applied Materials & Interfaces. 2014; 6(22) p. 20378-20384.
Mitra, et al., "Fluorescent in situ sequencing on polymerase colonies", Analytical Biochem. 2003;320, p. 55-65.
Nemoto, N., et al., "Fluorescence labeling of the C-terminus of proteins with a puromycin analogue in cell-free translation systems." FEBS letters. 1999; 462(1) p. 43-46.
Pan, H, et al., "A simple procedure to improve the surface passivation for single molecule fluorescence studies." Physical Biology. 2015; 12(4):045006.
Rothberg, JM, et al., "An integrated semiconductor device enabling non-optical genome sequencing." Nature. 2011;475(7356) p. 348-352.
Sharonov, A. et al., "Wide-field subdiffraction imaging by accumulated binding of diffusing probes." PNAS Dec. 12, 2006, vol. 103, No. 50, p. 18911-18916.
Shendure, et al., "The expanding scope of DNA sequencing." Nat Biotechnol. Nov. 2012; 30(11) p. 1084-1094.
Shendure. J, et al., "Advanced Sequencing Technologies: Methods and Goals." Nature Reviews Genetics. 2004;5(5) p. 335-344.
Sorgenfrei, S, et al., "Label-free field-effect-based single-molecule detection of DNA hybridization kinetics." Nat Nanotechnol. Feb. 2011 ; 6(2): p. 126-132.
Swaminathan, et al., "A theoretical justification for single molecule peptide sequencing." bioRxiv preprint doi: https://doi.org/10.1101/010587.
Tessler, et al., "Nanogel surface coatings for improved single-molecule imaging substrates." Journal of the Royal Society Interface. 2011;8 p. 1400-1408.
Tessler, L., et al. "Sensitive single-molecule protein quantification and protein complex detection in a microarray format." Proteomics. 2011; 11(24) p. 4731-4735.
Van Ginkel, et al., "Single-Molecule Peptide Fingerprinting." Biophysical Journal. 2017; 112(3):471a.
Van Oijen "Single-molecule approaches to characterizing kinetics of biomolecular interactions." AM. Current Opinion in Biotechnology, 2011;22(1) p. 75-80.
Xu, G, et al., "Chemoenzymatic labeling of protein C-termini for positive selection of C-terminal peptides." ACS Chemical Biology. 2011;6(10)p. 1015-1020.
Yao, et al., "Single-molecule protein sequencing through fingerprinting: computational assessment." Physical biology. 2015; 12(5):055003.

* cited by examiner

SINGLE MOLECULE PEPTIDE SEQUENCING METHODS

RELATED APPLICATIONS

This application claims benefit under 35 U.S.C. § 119(e) of U.S. Provisional application Ser. No. 62/864,051 filed Jun. 20, 2019, the disclosure of which is incorporated by reference herein in its entirety.

GOVERNMENT INTEREST

This invention was made with Government support under Grant Nos. NS087724 and U01 MH106011 awarded by the National Institutes of Health. The Government has certain rights in the invention.

FIELD OF THE INVENTION

This disclosure relates generally to methods of sequencing polypeptides.

BACKGROUND OF THE INVENTION

Massively parallel DNA sequencing has revolutionized the biological sciences [Shendure J, et al., Nature Reviews Genetics. 2004; 5(5):335-344 and Shendure J, & Aiden E L. Nature Biotech. 2012; 30(11):1084-1094], but no comparable technology exists for massively parallel sequencing of proteins. The most widely used DNA sequencing methods rely critically on the ability to locally amplify (i.e., copy) single DNA molecules—whether on a surface [Bentley D R, et al., Nature. 2008; 456(7218):53-59], attached to a bead [Brenner S, et al., Nature Biotechn. 2000; 18(6):630-634], or anchored inside a hydrogel matrix [Mitra R D, et al., Analytical Biochem. 2003; 320(1):55-65] to create a localized population of copies of the parent single DNA molecule. The copies can be probed in unison to achieve a strong, yet localized, fluorescent signal for readout via simple optics and standard cameras. For protein sequencing, on the other hand, there is no protein "copy machine" analogous to a DNA polymerase, which could perform such localized signal amplification.

Previously proposed approaches to massively parallel single molecule protein sequencing [Swaminathan J, et al., bioRxiv. 2014; p. 010587; Yao Y, et al., Physical biology. 2015; 12(5):055003; and van Ginkel J, et al., Biophysical Journal. 2017; 112(3):471a] utilize designs that rely on covalent chemical modification of specific amino acids along the chain. Such chain-internal tagging reactions are currently available only for a small subset of the 20 amino acids, and they have finite efficiency. Thus, such approaches are likely not able to read the identity of every amino acid along the chain. An alternative approach to protein sequencing [U.S. Pat. No. 9,435,810; Borgo B. & Havranek J J. Protein Science. 2014 2014 Dec. 16. doi: 10.1002/pro.26331; Tessler L A, et al., Journal of the Royal Society Interface. 2011; 8(63):1400-1408; and Borgo B. Theses and Dissertations (ETDs) at //openscholarship.wustl.edu/etd/1221. 2014] has been to use successive rounds of probing with N-terminal-specific amino-acid binders (NAABs) [U.S. Pat. No. 9,435,810]. Studies have proposed that proteins derived from N-terminal-specific enzymes such as aminopeptidases [Borgo B. & Havranek J J. Protein Science. 2014; 23(3):312-320], or from antibodies against the PITC-modified N-termini arising during Edman degradation [PCT Publication No. WO2010065531], could be used as NAABs for protein sequencing. For example certain prior methods [U.S. Pat. No. 9,435,810], utilize detection of specific binding of a high-specificity binding reagent with its target amino acid to determine if the N-terminal amino acid of a polypeptide is that specific target amino acid. This and other previous methods are limited in that they require highly specific, strong N-terminal binders for each of all 20 amino acids (and more if post-translational modifications, e.g., phosphorylation, are considered), which limits successful use of such methods. Protein sequencing remains truly a single molecule problem and efficient, reliable protein sequencing means have remained unavailable.

SUMMARY OF THE INVENTION

According to an aspect of the invention, a method of identifying an N-terminal amino acid of a polypeptide is provided, the method including (a) contacting a composition comprising a polypeptide with a set of independently selected N-terminal amino acid binding (NAAB) reagents, wherein a plurality of the independently selected NAAB reagents in the set bind to the polypeptide's N-terminal amino acid and the binding of each of the independently selected NAAB reagents to the polypeptide's N-terminal amino acid produces a specific detectable signal; (b) determining the specific detectable signal produced by the binding of each of the plurality of the independently selected NAAB reagents to the polypeptide's N-terminal amino acid; (c) kinetically measuring the determined specific detectable signals produced by the binding of the plurality of the independently selected NAAB reagents to the polypeptide's N-terminal amino acid; (d) combining the kinetic measurements; (e) determining a binding profile of the set of independently selected NAAB reagents based at least in part on the combined kinetic measurements; and (f) identifying the N-terminal amino acid in the polypeptide from the determined binding profile of the set of independently selected NAAB reagents. In certain embodiments, the detectable signal is a luminescent signal, and optionally is a fluorescent signal. In certain embodiments, the detectable signal is an electrical signal. In some embodiments, the detectable signal is detected using a single-photon avalanche diode (SPAD) detection method. In some embodiments, the method also includes removing the N-terminal amino acid from the polypeptide to reveal a next N-terminal amino acid on the polypeptide, and repeating the steps (a)-(f) to identify the next N-terminal amino acid of the polypeptide. In certain embodiments, the method also includes repeating the removal of the N-terminal amino acid and steps (a)-(f) a sufficient number of times to identify a portion or all of the polypeptide's amino acid sequence. In some embodiments, each of the independently selected NAAB reagents is a low affinity binding reagent for each of the polypeptide's amino acids. In some embodiments, each of the independently selected NAAB reagents is a low specificity binding reagent for each of the polypeptide's amino acids. In some embodiments, each of the independently selected NAAB reagents is not a high affinity binding reagent for any of the polypeptide's amino acids. In certain embodiments, each of the independently selected NAAB reagents is not a high specificity binding reagent for any of the polypeptide's amino acids. In some embodiments, the kinetic measuring comprises detecting a plurality of time-averaged specific detectable signals of each of the independently selected NAAB reagents that bind the polypeptide's N-terminal amino acid. In some embodiments, detecting the time-averaged signal comprises determining a length of time of the binding events of the independently selected NAAB reagents that bind the polypeptide's N-terminal amino acid. In certain embodiments, the plurality of the independently selected NAAB reagents in the set comprises at least 5, 10, 15, 20 or more different binding reagents. In some embodiments, a means of determining the specific detectable signals produced by the binding of each of the plurality of the independently selected NAAB reagents to the polypeptide's N-terminal amino acid comprises an optical detection method. In some embodiments, the optical detection method comprises microscopy. In certain embodiments, the microscopy comprises total internal reflection fluorescence (TIRF) microscopy. In certain embodiments, the TIRF microscopy comprises kinetically measuring the determined specific detectable signals produced by the binding of the plurality of the independently selected NAAB reagents to the polypeptide's N-terminal amino acid. In some embodiments, a means of determining the specific detectable signals produced by the binding of each of the plurality of the independently selected NAAB reagents to the polypeptide's N-terminal amino acid comprises an electrical detection method. In some embodiments, a means of determining the specific detectable signals produced by the binding of each of the plurality of the independently selected NAAB reagents to the polypeptide's N-terminal amino acid comprises a SPAD detection method. In some embodiments, more than one detectable signal produced by the binding of each of the plurality of the independently selected NAAB reagents to the polypeptide's N-terminal amino acid are simultaneously detected. In certain embodiments, the kinetically measuring comprises includes occupancy measurements of the binding kinetics of the NAAB reagents. In some embodiments, the kinetically measuring comprises affinity measurements of the binding kinetics of the NAAB reagents. In certain embodiments, a high-dimensional vector of kinetically-measured affinities for the N-terminal amino acid is produced from the kinetic measurements. In some embodiments, the N-terminal amino acid of the polypeptide is identified based, at least in part, on the high-dimensional vector of kinetically-measured affinities produced for the N-terminal amino acid. In some embodiments, the kinetically measuring comprises measuring using a high-time resolution measuring means capable of detecting individual binding and unbinding events. In certain embodiments, the kinetically measuring comprises measuring using a low-time resolution measuring means capable of detecting and integrating signals of many binding and unbinding events, wherein a binding affinity is deduced based on the detected time-averaged signals of the many binding and unbinding events. In some embodiments, the polypeptide is immobilized on a surface. In some embodiments, the polypeptide is immobilized in a manner to have, on average, no more than one peptide per a diffraction-limited spot. In some embodiments, a means for removing the N-terminal amino acid from the polypeptide comprises a cycle of Edman degradation. In certain embodiments, each of the independently selected N-terminal amino acid binding reagents is derived from an independently selected aminopeptidase. In some embodiments, each of the independently selected N-terminal amino acid binding reagents is derived from an independently selected tRNA synthetase. In certain embodiments, a plurality of specific detectable signals are simultaneously detected.

According to another aspect of the invention, a method of determining an amino acid sequence of a polypeptide is provided, the method including: (a) contacting a composition comprising a polypeptide with a set of independently selected N-terminal amino acid binding (NAAB) reagents, wherein a plurality of the independently selected NAAB reagents in the set bind to the polypeptide's N-terminal amino acid and the binding of each of the independently selected NAAB reagents to the polypeptide's N-terminal amino acid produces a specific detectable signal; (b) determining the specific detectable signal produced by the binding of each of the plurality of the independently selected NAAB reagents to the polypeptide's N-terminal amino acid; (c) kinetically measuring the determined specific detectable signals produced by the binding of the plurality of the independently selected NAAB reagents to the polypeptide's N-terminal amino acid; (d) combining the kinetic measurements; (e) determining a binding profile of the set of independently selected NAAB reagents based at least in part on the combined kinetic measurements; (f) identifying the N-terminal amino acid in the polypeptide from the determined binding profile of the set of independently selected NAAB reagents; (g) removing the identified N-terminal amino acid to reveal a next N-terminal polypeptide; and (h) repeating steps (a)-(g) on the next N-terminal amino acid of the polypeptide to determine a partial or full amino acid sequence of the polypeptide. In some embodiments, the detectable signal is a luminescent signal, and optionally is a fluorescent signal. In some embodiments, the detectable signal is an electrical signal. In certain embodiments, the detectable signal is detected using a single-photon avalanche diode (SPAD) detection method. In some embodiments, each of the independently selected NAAB reagents is a low affinity binding reagent for each of the polypeptide's amino acids. In some embodiments, each of the independently selected NAAB reagents is a low specificity binding reagent for each of the polypeptide's amino acids. In certain embodiments, each of the independently selected NAAB reagents is not a high affinity binding reagent for any of the polypeptide's amino acids. In some embodiments, each of the independently selected NAAB reagents is not a high specificity binding reagent for any of the polypeptide's amino acids. In some embodiments, the kinetic measuring comprises detecting a plurality of time-averaged specific detectable signals of each of the independently selected NAAB reagents that bind the polypeptide's N-terminal amino acid. In certain embodiments, detecting the time-averaged signal comprises determining a length of time of the binding events of the independently selected NAAB reagents that bind the polypeptide's N-terminal amino acid. In some embodiments, the plurality of the independently selected NAAB reagents in the set comprises at least 5, 10, 15, 20 or more different binding reagents. In some embodiments, a means of determining the specific detectable signals produced by the binding of each of the plurality of the independently selected NAAB reagents to the polypeptide's N-terminal amino acid comprises an optical detection method. In some embodiments, the optical detection method comprises microscopy. In certain embodiments, the microscopy comprises total internal reflection fluorescence (TIRF) microscopy. In certain embodiments, the TIRF microscopy comprises kinetically measuring the determined specific detectable signals produced by the binding of the plurality of the independently selected NAAB reagents to the polypeptide's N-terminal amino acid. In some embodiments, a means of determining the specific detectable signals produced by the binding of each of the plurality of the independently selected NAAB reagents to the polypeptide's N-terminal amino acid comprises an electrical detection method. In some embodiments, a means of determining the specific detectable signals produced by the binding of each of the plurality of the independently selected NAAB reagents to the polypeptide's N-terminal amino acid comprises a SPAD detection method. In certain embodiments, more than one detectable signal produced by the binding of each of the plurality of the independently selected NAAB reagents to the polypeptide's N-terminal amino acid are simultaneously detected. In some embodiments, the kinetically measuring comprises includes occupancy measurements of the binding kinetics of the NAAB reagents. In some embodiments, the kinetically measuring comprises affinity measurements of the binding kinetics of the NAAB reagents. In some embodiments, a high-dimensional vector of kinetically-measured affinities for the N-terminal amino acid is produced from the kinetic measurements. In certain embodiments, the N-terminal amino acid of the polypeptide is identified based, at least in part, on the high-dimensional vector of kinetically-measured affinities produced for the N-terminal amino acid. In some embodiments, the kinetically measuring comprises measuring using a high-time resolution measuring means capable of detecting individual binding and unbinding events. In some embodiments, the kinetically measuring comprises measuring using a low-time resolution measuring means capable of detecting and integrating signals of many binding and unbinding events, wherein a binding affinity is deduced based on the detected time-averaged signals of the many binding and unbinding events. In certain embodiments, the polypeptide is immobilized on a surface. In some embodiments, the polypeptide is immobilized in a manner to have, on average, no more than one peptide per a diffraction-limited spot. In some embodiments, a means for removing the N-terminal amino acid from the polypeptide comprises a cycle of Edman degradation. In some embodiments, each of the independently selected N-terminal amino acid binding reagents is derived from an independently selected aminopeptidase. In certain embodiments, each of the independently selected N-terminal amino acid binding reagents is derived from an independently selected tRNA synthetase.

According to another aspect of the invention, a method of spectral sequencing a peptide is provided, the method including (a) measuring one or more of probe-target binding affinities and probe-target binding kinetics of a plurality of low-affinity, relatively non-specific N-terminal-specific amino-acid binders (NAABs) and amino acid targets, (b) collectively determining a spectrum of affinity across the NAABs, for each of the N-terminal amino acid targets, (c) determining the identity of the N-terminal amino acids based on the collectively determined spectrum of affinity across the NAABs; and (d) sequencing a peptide based on the determined identities of the N-termination amino acids. In some embodiments, the identity spectrum of affinity across the NAABs is used to determine a specific profile of affinity of one or more of the NAABs. In certain embodiments, a means for the measuring of the binding affinities of the plurality of the low-affinity, relatively non-specific NAABs comprises measuring the single molecule binding kinetics in a massively parallel fashion. In some embodiments, a means for the measuring of the single molecule binding kinetics comprises applying a Points Accumulation for Imaging in Nanoscale Topography (PAINT) technique to the NAABs. In some embodiments, the method also includes using a plurality of randomized NAAB affinity matrices and an affinity matrix derived directly from the collectively determined spectrum of affinity across the NAABs, to sequence a single peptide. In certain embodiments, a means of the measuring one or more of probe-target binding affinities and probe-target binding kinetics, comprises single-molecule fluorescence based measurement of probe-target binding.

According to another aspect of the invention, a method of peptide sequencing is provided, the method including: (a) utilizing a non-optimized plurality of low-affinity amino acid binders to identify an N-terminal amino acid in a peptide; (b) removing the N-terminal amino acid in the peptide thereby exposing a subsequent N-terminal amino acid in the peptide; and (c) utilizing the non-optimized plurality of low-affinity amino acid binders to identify the subsequent N-terminal amino acid in the peptide. In some embodiments, the method also includes repeating steps (b) and (c).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows a measurement approach in which the target (green disk) is attached to a glass slide and observed using total internal reflection fluorescence (TIRF) microscopy. N-terminal-specific amino-acid (NAAB) binders (brown clefts) bearing fluorophores (red dots) are excited by a TIRF beam (purple) and generate fluorescent photon emissions (red waves). FIG. 1B shows that when a fluorophore is bound, there is an increase in fluorescence in the spot containing the target. Photobleaching of the fluorophore is indistinguishable from unbinding events, so it is important to use a dye that is robust against photobleaching. The plot shows an illustrative stochastic kinetics simulation incorporating Poisson shot noise of photon emission. FIG. 1C is a plot showing the affinities of the methionine targeting and tryptophan targeting NAABs for each of the natural amino acids excluding cysteine (black Xs). Upon measuring the affinities for these NAABs against an unknown target, the target can be identified with the amino acid corresponding to the colored region within which the plotted affinities fall. As an example, a pair of measurements yielding the white star would identify the target as glycine. FIG. 1D is a plot showing the affinities of the glutamine and lysine targeting NAABs for each of the amino acids. Some amino acids that are practically indistinguishable using the Met and Trp NAABs are easily distinguished using the Gln and Lys NAABs. As an example, if the same target amino acid described in FIG. 1C were measured with only the Gln and Lys NAABs, yielding the white star, the target would be identified as proline. However, combining these measurements with those for the white star in FIG. 1C with Met and Trp NAABs, it is seen that the true identity of the target is serine. Thus, the higher dimensional measurement of the amino acid using many different NAABs allows disambiguation of the amino acid identity.

FIG. 2A illustrates how a measurement performed using the proposed scheme yields a fluorescence intensity trace where periods of high intensity correspond to the target being bound and periods of low intensity correspond to the target being free. The affinity of a binder against the target can then be determined in two ways, either via occupancy measurements or via luminosity measurements. FIG. 2B illustrates a luminosity measurement that is performed "along the brightness axis," by calculating $k_D$ directly from the average luminosity of the target over the whole observation period. FIG. 2C illustrates an occupancy measurement performed "along the time axis," by calculating $k_{on}$ from the average time between binding events, and $k_{off}$ from the average length of binding events. FIG. 2D shows validation of the simulation by applying occupancy measurements to determine $k_{on}$ and $k_{on}$ from simulated data. The parameters used were identical to those used in FIG. 2a of Jungmann, et al., Nano Letters. 2010; 10(11):4756-4761. See text for symbol definitions.

FIG. 3A illustrates accuracies of occupation measurements of $k_D$ are shown as a function of $k_D$ and $k_{on}$ for the simulation described in the text, with $T_{exp}=100$ s. These measurements achieve high accuracy for $k_{on} \geq 10^5$ m$^{-1}$ s$^{-1}$ and $k_{off} \ll 100$ s$^{-1}$. For values of $k_{off}$ on the order of 100 s$^{-1}$ (upper right-hand corner), the accuracy deteriorates significantly. In FIG. 3B the accuracies of luminosity measurements of $k_D$ are shown as a function of $k_D$ and $k_{on}$. These measurements achieve high accuracy for $k_{on} \geq 10^5$ m$^{-1}$ s$^{-1}$ and $k_D \geq 100$ nm. The heat map shown gives the fractional errors as a function of $k_D$ and $k_{on}$ for the simulation described in the text, with $T_{exp}=100$ s. In contrast to occupation measurements, the accuracy of luminosity measurements does not deteriorate for very high values of $k_{off}$. FIG. 3C illustrates for luminosity measurements only, the mean fractional error in the measured value of $k_D$ plotted as a function of the observation time for five different values of $k_D$. The line y=1/x is plotted as a guide to the eye. For $k_D=10$ nm and $k_D=100$ nm, the effects of photobleaching are evident at longer runtimes. FIG. 3D shows for luminosity measurements only, the measured value of $k_D$ plotted as a function of the actual value of $k_D$ for 8 different values of the runtime. The performance of the algorithm improves dramatically for $\tau_{obs}>25$ s. The line y=x is plotted as a guide to the eye. Error bars in FIGS. 3C & D denote standard error over 100 trials.

FIG. 4A-D provides heat maps demonstrating that methods identification of amino acids are robust against systematic error. The fraction of amino acids incorrectly identified is plotted as a function of $\tau_{obs}$ for four different values of the systematic calibration error $\sigma_C$ and four different values of the systematic kinetic error $\sigma_K$ (as described in the text). FIG. 4A illustrates that in the absence of systematic error, measurements with $\tau_{obs}=50$ s result in correct amino acid identification more than 98% of the time. For 25% error in $k_D$, the accuracy drops to 97.5%, and if 5% calibration error is added, it drops further to 92%. More than 5% systematic error in the calibration leads to very significant numbers of mistakes in amino acid identification. FIG. 4B illustrates that with $\tau_{obs}=100$ s, an accuracy of 97.5% was obtained for 25% error in $k_D$ and 5% error in the calibration. FIG. 4C illustrates that increasing $\tau_{obs}$ beyond 100 s at the same binder concentration leads to diminishing improvements in the accuracy. FIG. 4D illustrates that the sensitivity to calibration error could be substantially reduced by decreasing the concentration of free binders to 100 nm. However, this increased concentration necessitates a longer runtime.

DETAILED DESCRIPTION AND EXAMPLES

Figure 1A:
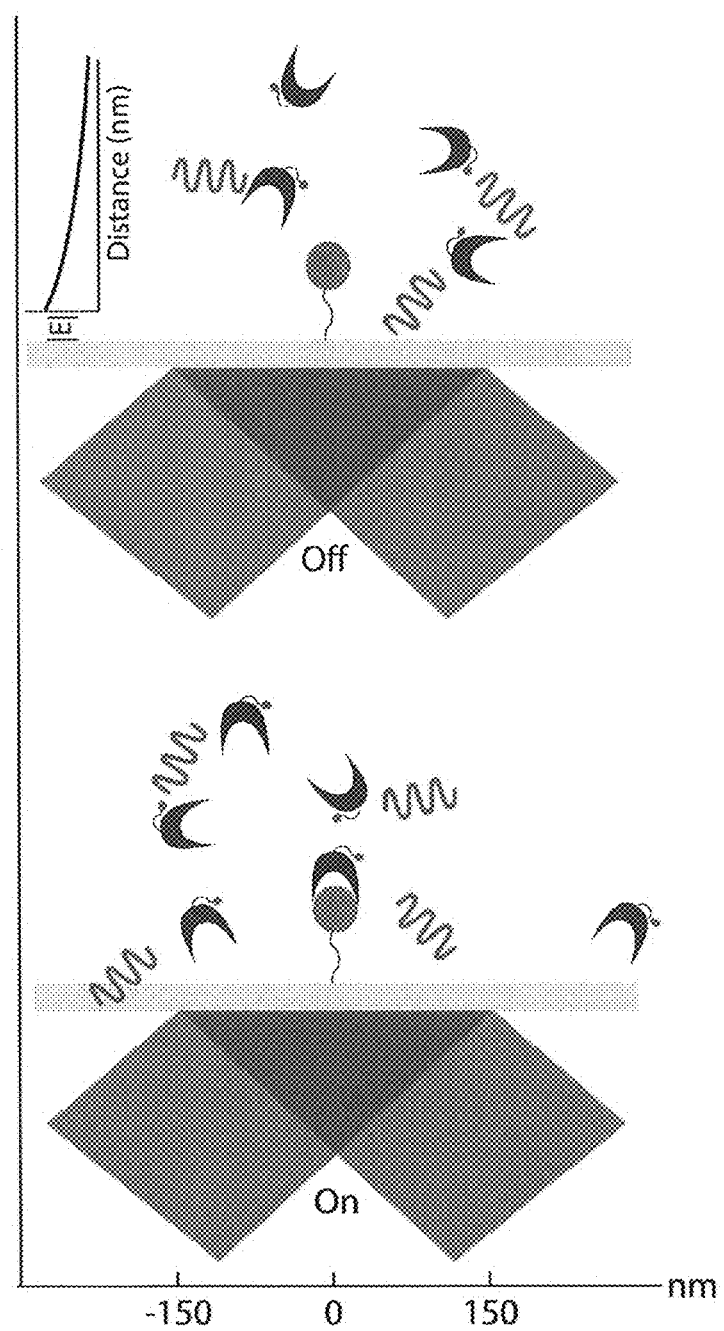
FIG. 1A-D shows schematic diagrams and an emission plot illustrating a process of identifying amino acids using kinetic measurements.

Instead of attempting to improve properties of N-terminal-specific amino-acid binders (NAABs), a strategy has now been determined, referred to herein as "spectral sequencing" that avoids limitations of existing NAABs and enables single molecule protein sequencing without a need to design or develop novel binding reagents. Spectral sequencing measures the affinities of many low-affinity, relatively non-specific NAABs, collectively determining a "spectrum" or "profile" of affinity across binders, for each of the N-terminal amino acids. This profile is sufficient to determine the identity of the N-terminal amino acid. Thus, rather than requiring individual binders to be specific in and of themselves, methods of the invention can be used to infer a specific profile by combining measurements of many non-specific interactions. The spectral sequencing approach of the invention measures the single molecule binding kinetics in a massively parallel fashion, using a generalization of Points Accumulation for Imaging in Nanoscale Topography (PAINT) techniques [Sharonov A, & Hochstrasser R M. PNAS. 2006; 103(50):18911-18916 and Jungmann R, et al., Nano letters. 2010; 10(11):4756-4761] to N-terminal amino acid binders.

Studies have been performed to derive the capabilities of single-molecule fluorescence based measurement of probe binding kinetics as a function of probe properties and noise sources. This analysis has been applied to the problem of sequencing proteins by measuring profiles of NAAB binding kinetics. Using a range of randomized NAAB affinity matrices as well as an affinity matrix derived directly from the existing measured NAAB kinetics [U.S. Pat. No. 9,435,810], sequencing of single peptides has been simulated and resulted in 97.5% percent accuracy in amino acid identification over a total observation period of 35 minutes, even in the presence of up to 5% percent error in the instrument calibration and 25% variation in the true underlying kinetics of the binders, due for example to the effects of non-terminal amino acids.

A method of single molecule sequencing of polypeptides has now been identified. In addition to permitting sequencing of single polypeptides, embodiments of the invention can also be used for massively parallel N-terminal amino acid identification and sequencing of polypeptides. Unlike previous approaches, methods of the invention are robust to both weak and non-specific probe-target affinities, a feature that demonstrated herein by applying the method to a range of randomized affinity matrices consisting of relatively low-quality binders. Methods of the invention support a novel principle for proteomic measurement whereby highly non-optimized sets of low-affinity binders can be utilized for protein sequencing, thus shifting the burden of amino acid identification from biomolecular design to readout. Measurement of probe occupancy times, or of time-averaged fluorescence, are utilized in methods of the invention to allow high-accuracy determination of N-terminal amino acid identity using non-specific probe sets. In one embodiment of the invention, a time-averaged fluorescence method is used and scales well to extremely weak-binding probes.

Certain embodiments of the invention can provide single amino acid resolution and the ability to distinguish many canonical and modified amino acids, even using highly non-optimized probe sets. This readout method expands the design space for single molecule peptide sequencing by removing constraints on the properties of the binding probes.

Methods of the invention have simplified and resolved certain problems of previous single molecule protein sequencing methods. Methods for peptide sequence presented herein are supported by assessment and analysis of the sequencing approach of the invention, which utilizes low-affinity, low-specificity binding reagents, which differs significantly from previous methods such as those described in U.S. Pat. No. 9,435,810, in which specific binding of a high-specificity binding reagent with its target amino acid is used to identify if that target amino acid is the N-terminal amino acid of a polypeptide. Studies and simulations have now demonstrated that embodiments of methods of the invention can permit protein sequencing without previous difficulties associated with generating a high-quality library of binding reagents that each selectively bind to N-terminal amino acids of polypeptides.

Compositions, Peptides, and Amino Acids

Certain embodiments of methods of the invention may be carried out in a composition that comprises at least one polypeptide. The term "composition" as used herein in reference to a method carried out on a polypeptide of interest may refer to a physical environment of the polypeptide. As used herein the term "polypeptide of interest" means a polypeptide that is sequenced entirely or in part by a method of the invention. In non-limiting examples, a composition comprising the polypeptide may comprise one or more of: a container, a dish, a vial, a tube, a microscope slide, a fluid, a surface, or any other suitable physical environment suitable for use in a method of the invention. In some embodiments, a composition comprises a polypeptide is attached to a surface, which also referred to herein as "immobilized on" a surface. It will be understood that the term "contacting a composition comprising a polypeptide" as used herein in reference to a method of the invention means that the polypeptide is contacted.

Methods of the invention can be used to determine all or a portion of the amino acid sequence of a polypeptide that includes naturally occurring or modified amino acids. The twenty natural-occurring amino acids include: Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). It will be understood that methods of the invention can also be used for sequencing all or a portion of peptides that include one or more non-natural amino acids. The terms "peptide" and "polypeptide" are used interchangeably herein.

N-Terminal Amino Acid Binding (NAAB) Reagents

Methods of the invention include the use of sets of binding reagents in which some or all of the binding reagents are low-affinity and/or low-specificity binding reagents for amino acids. The term "binding reagent" used in reference to a method of the invention means an N-terminal amino acid binding (NAAB) reagent, which may also be referred to interchangeably as an "NAAB". It will be understood that an NAAB reagent may be in a solution comprising one or more of a solvent, a degradation reagent, a buffer, etc. Suitable solutions and components thereof for use in methods of the invention can be selected by a practitioner based the disclosure provided herein and art-known components and methods. NAAB reagents of the invention are reagents that bind to N-terminal amino acids of polypeptides. An NAAB reagent of the invention may be prepared by modifying a naturally occurring protein to include one or more mutations in the amino acid sequence thereby producing an engineered protein that binds N-terminal amino acids in a low. For example, aminopeptidases or tRNA synthetases can be modified to create NAAB reagents that selectively bind to particular N-terminal amino acids in a low-affinity and/or low-specificity manner. In some embodiments of the invention, one or more of the independently selected NAAB reagents is derived from an independently selected aminopeptidase. In certain embodiments of the invention, one or more of the independently selected NAAB reagents is derived from an independently selected tRNA synthetase.

It will be understood that an NAAB reagent used in an embodiment of the invention can be prepared using various means. A non-limiting example of preparing an NAAB reagent of the invention includes cloning its encoding sequence into an expression vector, expressing in a host cell (e.g., in an *E. coli* cell), purifying the expression product, and assaying the produced NAAB reagent for low-affinity and/or low-specificity binding to an N-terminal amino acid of a polypeptide. In a non-limiting example, a binding activity of a prepared NAAB can be assayed against a standard set of polypeptides having different N-terminal residues. In some embodiments of the invention, an NAAB reagent is a synthetic or recombinant NAAB reagent. Suitable low-affinity and/or low specificity NAABs are known in the art, with non-limiting examples such as NAAB reagents set forth in U.S. Pat. No. 9,435,810, which also describes methods of preparing NAAB reagents and assays with which to assess a level of specificity of a prepared NAAB reagent.

Overview of Certain Sequencing Methods

Methods of the invention include contacting a polypeptide with a set of independently selected NAAB reagents. As used herein the term "set" indicates at least 2, 3, 4, 5, 6, 7, 8, 9, 10, 11, 12, 13, 14, 15, 16, 17, 18, 19, 20, 21, 22, 23, 24, 25, or more independently selected NAAB reagents. The term "independently selected" as used herein in reference to binding reagents means that each of the binding reagents in the set may be individually chosen for inclusion in the set, and as a result, a set of independently selected NAAB reagents may include 2, 3, 4, 5, 6, 7, 8, 9, 10, 11, 12, 13, 14, 15, 16, 17, 18, 19, 20, 21, 22, 23, 24, 25 or more different NAAB binding reagents.

In certain embodiments of methods of the invention, a polypeptide of interest is contacted with two or more NAAB reagents capable of binding to more than one N-terminal amino acid. An NAAB reagent used in a method of the invention may be selected in part due to its capability to bind an N-terminal amino acid with a low binding affinity and/or a low binding specificity. In some embodiments of the invention, the NAAB reagents in the set of reagents that contacts a polypeptide of interest are NAAB reagents that do not each selectively bind to a particular amino acid. In certain embodiments of the invention none of the plurality of NAABs selectively bind an N-terminal amino acid of a polypeptide of interest. Certain independently selected NAAB reagents when contacted with a peptide in a method of the invention are capable of binding 2, 3, 4, 5, 6, 7, 8, 9, 10, 11, 12, 13, 14, 15, 16, 17, 18, 19, 20, or more different N-terminal amino acids with one or more low binding affinities and/or low binding specificities. Thus, an independently selected NAAB reagent may bind more than one amino acid that is in the N-terminal position of a polypeptide. Methods of the invention include contacting a polypeptide of interest with a set of independently selected NAABs in which a plurality of the NAABs bind the N-terminal amino acid of the polypeptide, meaning that more than one of the set of binding agents binds to the N-terminal amino acid in the polypeptide. As used herein the term "plurality" means more than 1, which may be 2, 3, 4, 5, 6, 7, 8, 9, 10, 11, 12, 13, 14, 15, 16, 17, 18, 19, 20, or more.

In certain methods of the invention, when a peptide is contacted with a set of independently selected binding reagents, each binding (also referred to herein as a "binding event"), of one of the set of binding reagents with the peptide's N-terminal amino acid results in a specific detectable signal. Thus, in practice, contacting the peptide with a set of NAAB reagents of which a plurality bind the N-terminal amino acid of the polypeptide, results in a plurality of specific detectable signals. Methods of the invention do not include detecting only a detectable signal resulting from a single NAAB, but includes detecting a plurality of detectable signals resulting from the plurality of the NAABs.

Methods of the invention comprise determining the plurality of specific detectable signals that are produced by the binding of the plurality of the independently selected NAAB reagents to the polypeptide's N-terminal amino acid. A detectable signal may, in some embodiments be a visual or optically detectable signal, such as luminescence. With respect to luminescence, in some embodiments determining comprises detecting the presence of a luminescent signal indicating binding of an NAAB with an N-termination amino acid. A non-limiting example of a luminescent signal that may be used in a method of the invention is a fluorescent signal. Preparation and use of fluorescent signals to detect binding are routinely practiced in the art. Other types of detectable signals that may be used in certain embodiments of the invention include but are not limited to: electrical signals and chemical signals, etc.

The determination of the detectable signals that result from binding of NAAB reagents with N-terminal amino acids provides information for measurement of single binding kinetics in a massively parallel manner. A non-limiting example of kinetic measurement comprises detecting a plurality of time-averaged specific detectable signals of each of the independently selected NAAB reagents that bind the polypeptide's N-terminal amino acid. In some embodiments of methods of the invention, detecting a time-averaged signal includes determining a length of time of binding events of the independently selected NAAB reagents that bind the polypeptide's N-terminal amino acid. Additional details of kinetic measurement are provided elsewhere herein.

Kinetic measurements of binding events between the N-terminal amino acid of a peptide of interest and a plurality of NAAB reagents can be combined to prepare a binding profile of the plurality of NAAB reagents, and, in certain embodiments, a binding profile of the set of NAAB reagents contacted with the peptide of interest. As described in additional detail herein, the profile of the binding of the independently selected NAAB reagents can be used to identify the N-terminal amino acid of the peptide that was contacted.

Different means of determining a detectable signal can be used in methods of the invention. In a non-limiting example, an optical detection method can be used, which in some instances includes microscopy. In some embodiments of the invention, total internal reflection fluorescence (TIRF) microscopy is used in methods to determine a detectable signal. TIRF microscopy, and other suitable methods, can be used to kinetically measure the determined specific detectable signals produced by binding of the plurality of the independently selected NAAB reagents to the peptide's N-terminal amino acid. Data obtained with the kinetic measurements can be used to produce a high-dimensional vector of kinetically-measured affinities of individually selected NAAB reagents for the N-terminal amino acid, and such vectors can be used in identifying the N-terminal amino acid of the contacted peptide. As used herein the terms "kinetically measure" or "kinetically measuring" mean measuring using one or more of the following means: (1) measuring with high time resolution so one can detect individual binding and unbinding events and determine binding affinities and (2) measuring with low time resolution, to integrate the luminescence over many binding and unbinding events and deduce binding affinity based on the time-averaged luminescence. For example though not intended to be limiting, a measurement using means (1) includes detecting/seeing changes in intensity at a peptide location at high time resolution which permits detection of fluctuations in the signal from the NAAB as it binds on and off over time, then the amount of time the NAAB spends bound versus unbound can be compared by analyzing the time series of photon counts from the detector/pixel. In some embodiments of the invention kinetic measurement using means (1) and means (2) are performed at the same time, because it is possible to obtain low-time-resolution data by averaging over high-time-resolution data. In some embodiments, low-time-resolution measurements are performed in conjunction with us of a camera such as a CCD camera. In certain embodiments of the invention high-time-resolution measurements are performed in conjunction with use of a camera such as a CMOS camera.

Methods of the invention can be used to identify one or more amino acids in a peptide sequence. For example, one round or cycle of identifying the N-terminal amino acid of a peptide of interest, yields an identity of the single N-terminal amino acid. Successive rounds or cycles of methods of the invention can be carried in which a first N-terminal amino acid is identified, that N-terminal amino acid is removed revealing a new N-terminal amino acid, and the new N-terminal amino acid is identified using methods of the invention. Art-known methods can be used in embodiments of methods of the invention to remove an N-terminal amino acid from a peptide. A non-limiting example of a suitable method for removing an N-terminal amino acid from a polypeptide comprises a cycle of Edman degradation. It will be understood that a method of the invention may include repeating removal of the N-terminal amino acid a sufficient number of times to identify of the amino acids in the polypeptide's sequence. In some embodiments of methods of the invention, protein/peptide degradation may take place at essentially the same time as the luminescence measurements. For example, in some embodiments of methods of the invention a solution comprising the NAAB reagents also includes one or more degradation reagents, therefore permitting both obtaining luminescence measurements and removal of an N-terminal amino acid to occur. It will be understood that in certain embodiments of methods of the invention, more than one fluorescent signal is measured simultaneously.

Studies and Analysis

Simulation studies have now been performed to assess approaches to massively parallel single molecule protein sequencing. Certain strategies assessed in the studies included ones in which a set of peptides was immobilized on a surface and imaged using total internal reflection fluorescence (TIRF) microscopy. Non-limiting examples of detection means that may be used in embodiments of methods of the invention are: TIRF microscopy, electric-readout detection means, and single-photon avalanche diode (SPAD) detection means. Art-known detection methods and protocols for using TIRF, electric-readout detection, and SPAD may be used in conjunction with methods of the invention disclosed herein.

In some embodiments of the invention, a peptide to be single-molecule sequenced using a method of the invention is immobilized on a surface in a manner to have, on average, no more than one peptide per diffraction-limited spot (e.g. spot containing the target). This positioning results in the ability to individually resolve each peptide with microscopy and for imagining single-molecule protein sequencing.

Art-known methods have been identified for use to appropriately passivate the attachment surface to minimize non-specific binding [see for example Tessler L A, et al., Journal of the Royal Society Interface. 2011; 8(63):1400-1408; Tessler L A. & Mitra R D. Proteomics. 2011; 11(24):4731-4735; Chandradoss S D et al., Journal of Visualized Experiments: JoVE. 2014; (86); Selvin P R. & Ha T. in Cold Spring Harbor Laboratory Press; Edited by Paul R. Selvin; 2008; Joo C, et al, Trends in Biochemical Sciences. 2013; 38(1): 30-37; Groll J. & Moeller M. in: Methods in Enzymology. vol. 472. Elsevier; 2010. p. 1-18; Finkelstein U. & Greene E C. In: DNA Recombination. Springer; 2011. p. 447-461; and Pan H, et al., Physical Biology. 2015; 12(4):045006]. It was identified that the limited vertical extent of the evanescent excitation field of the TIRF microscope allows differential sensitivity to fluorescent molecules that are near the microscope slide surface, which allows detection of NAABs that have bound to peptides on the surface. Existing sets of NAABS (e.g. [U.S. Pat. No. 9,435,810]), derived from aminopeptidases or tRNA synthetases that have affinities biased towards specific amino acids, have low affinity or specificity, so one cannot deduce the identity of an N-terminal amino acid from the binding of a single NAAB. Instead, methods of the invention are designed to deduce the identity of the N terminal amino acid of a particular peptide by measuring the binding kinetics of a set of NAABs against the peptide. After observing the binding of each of a set of NAAB reagents against the peptide, a cycle of Edman degradation [Edman P, et al. Acta Chem Scand. 1950; 4(7):283-293 and Laursen R A. The FEBS Journal. 1971; 20(1):89-102] is carried out, revealing the next amino acid along the chain as the new N-terminus, and then the process is repeated.

Figure 1B:
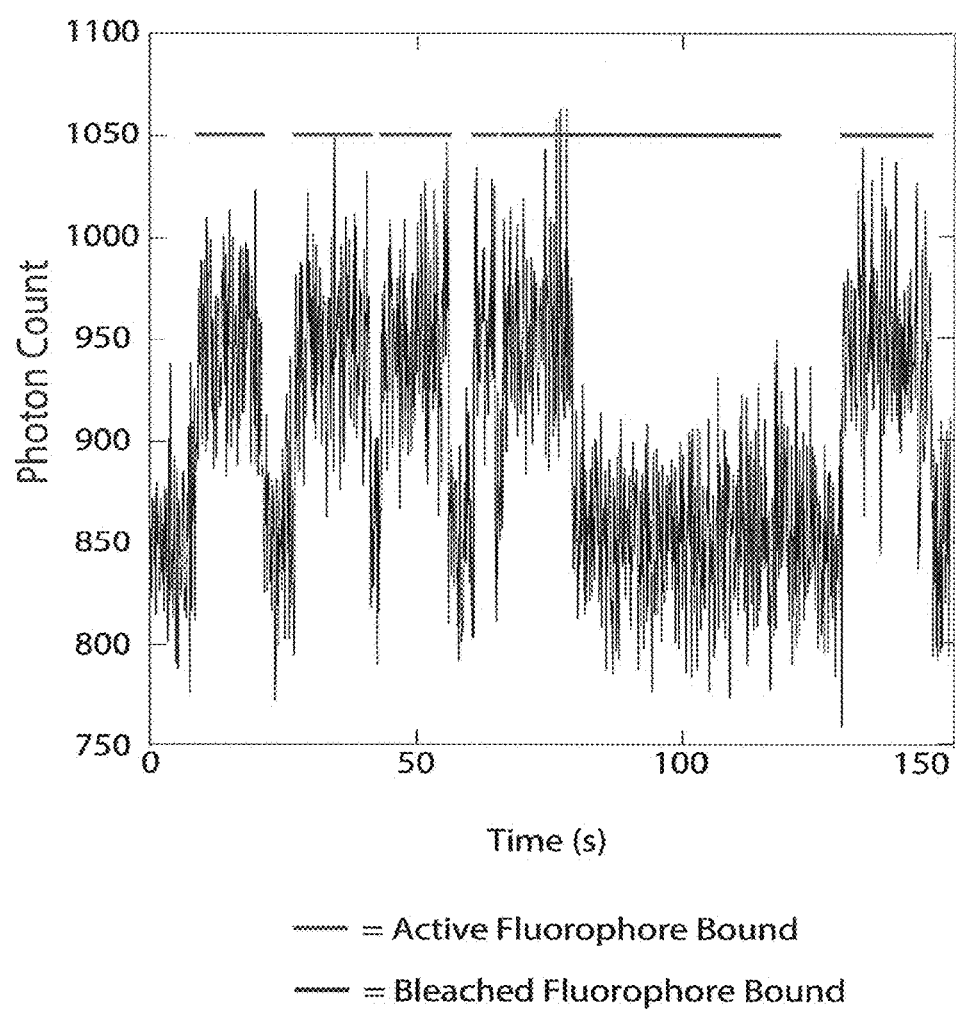
Figure 1C:
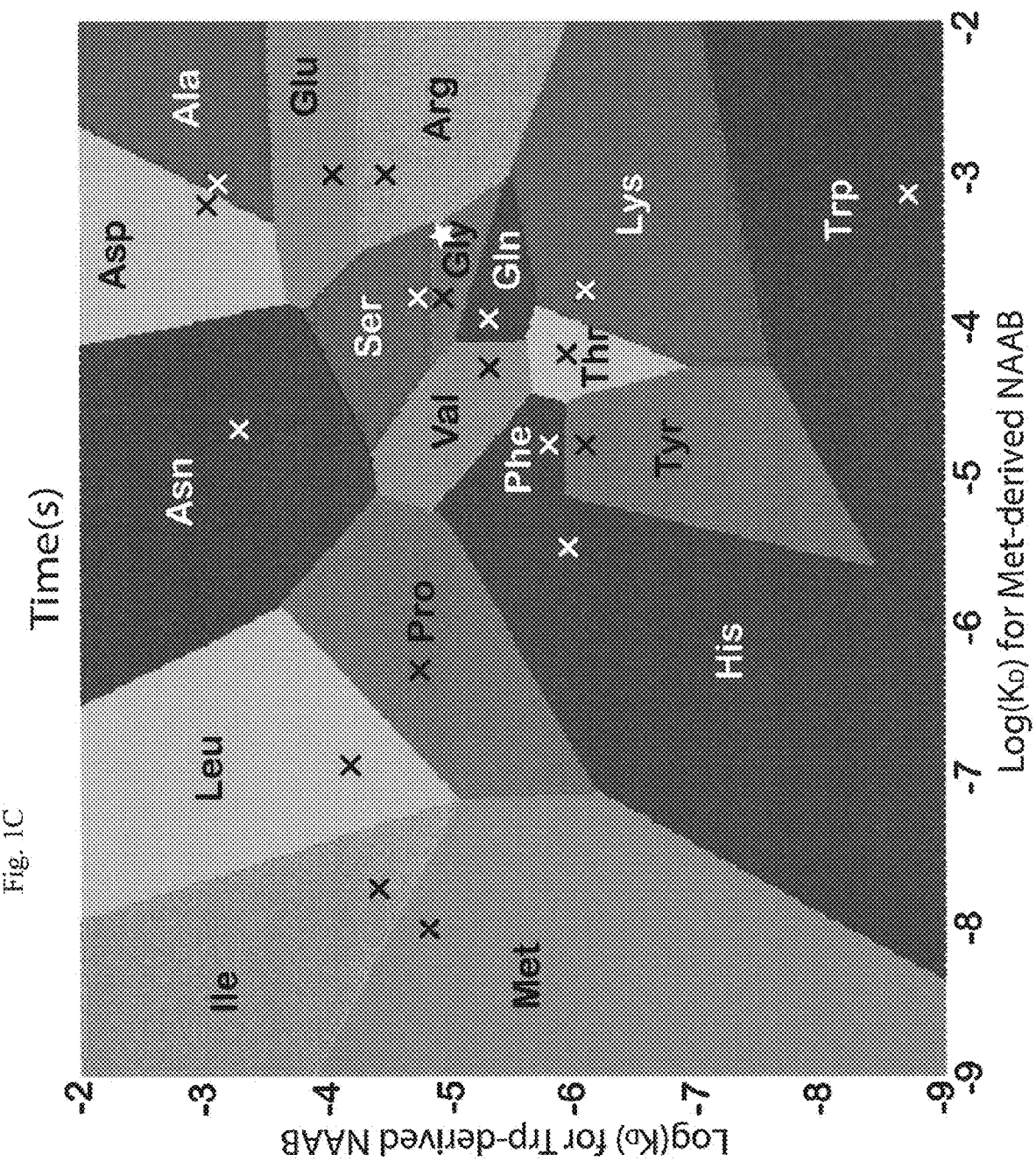
Figure 1D:
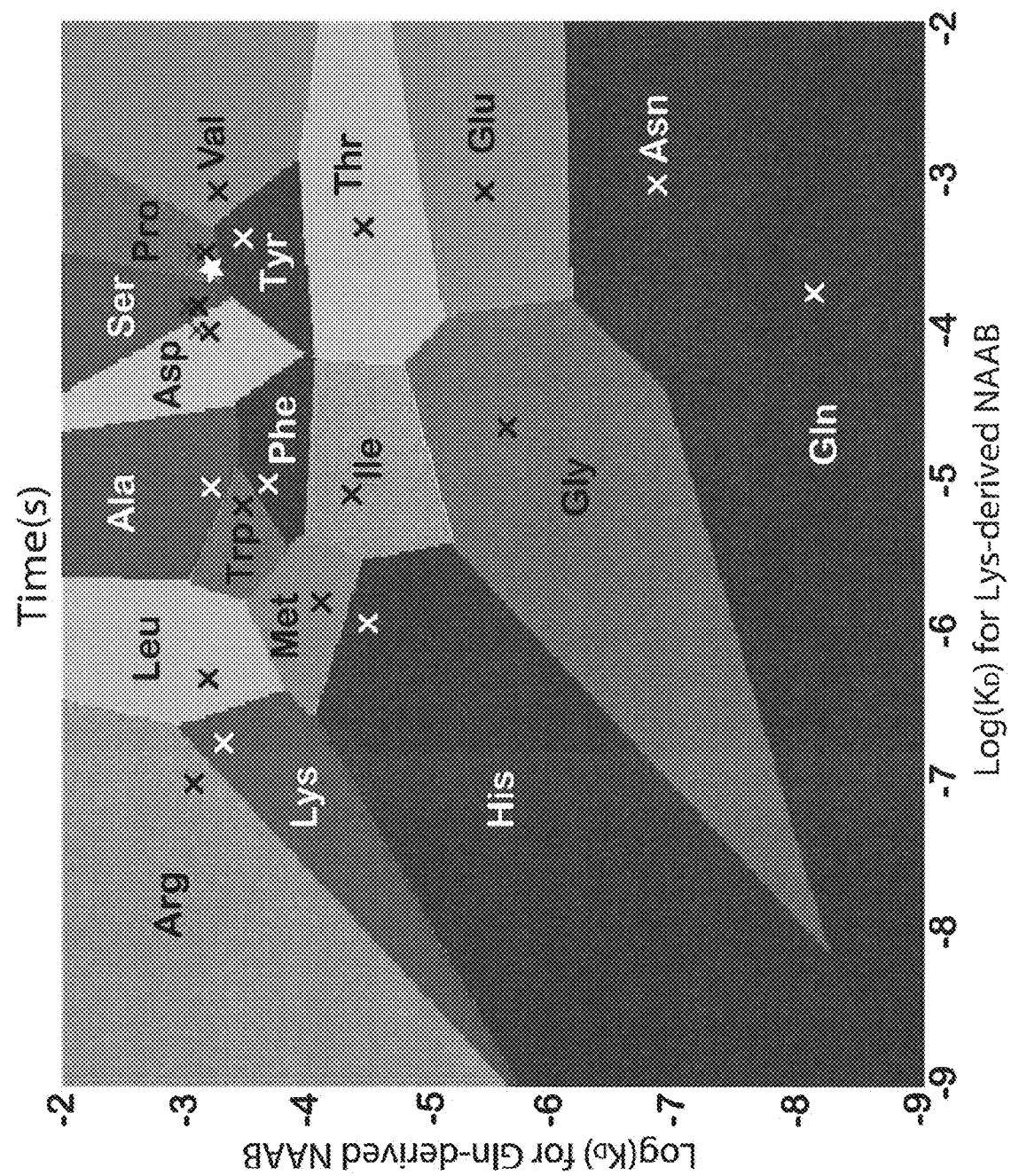

A process of the invention to observe binding kinetics with TIRF microscopy (FIG. 1A-B) is similar to that used in Points Accumulation for Imaging of Nanoscale Topography (PAINT [Sharonov A. & Hochstrasser R M. PNAS. 2006; 103(50):18911-18916]), 70 e.g., DNA PAINT [Jungmann R, et al., Nano letters. 2010; 10(11):4756-4761]. This process produces a high-dimensional vector of kinetically-measured affinities at each cycle (FIG. 1C-D) that can be used to infer the N-terminal amino acid. This previously known method, although potentially applicable for current NAABs, ultimately breaks down for probes whose binding is extremely weak, i.e., for which the bound time is so short that only a small number of photons is released while the probe is bound. Although fast camera frame rates can be used, the prior system ultimately becomes limited in the achievable fluorescent signal to noise ratio, unless the measurements are averaged over long experiment times. To extend these concepts into the ultra-weak binding regime, methods of the invention are tested that do not measure the precise binding and unbinding kinetics but rather the time-averaged luminosity of each spot, which indicates the fraction of time a probe was bound. It is identified that this type of luminosity-based measurement method f the invention is highly robust and compatible with short run times. As indicated elsewhere herein, in addition to the use of TIRF microscopy to determine binding kinetics, detection means that may be used in some embodiments of the invention, include use of one or more of electric-readout detection means and single-photon avalanche diode (SPAD) detection means.

Experimental Approaches

The experimental approach included three sections: (1) regimes of binder concentration and illumination intensity within which one would expect the proposed method to operate were considered; (2) two possible methods for analyzing single molecule kinetic data are described and discussed; and (3) simulations were performed using the derived parameters and data analysis methods in order to estimate the sensitivity of an embodiment of a sequencing method of the invention.

Distinguishability of Amino Acids Based on their NAAB Binding Profiles

A set of binders (NAABs) is characterized by their affinities for their targets (e.g., the 20 amino acids), which can be expressed in the form of an affinity matrix. The affinity matrix A is defined such that the i,jth entry of A is the negative log affinity of the ith binder for the jth target:

$$a_{i,j} = -\log(k_D), \quad (1)$$

where $k_D$ is the dissociation constant (TD is defined as the dissociation time).

Values of the affinities encoded in the affinity matrix are referred to herein as the "reference values," to distinguish them from the "measured" values obtained in the experiment and from the "true" values, which may depend on environmental conditions but which are not known by the experimenter; the reference values are known and used in the computational process of identifying amino acids. As shown elsewhere herein, it is estimated that it would be possible to determine the identities of the N-terminal amino acids from affinity measurements with 99% accuracy, provided that the affinity measurements occur according to a distribution centered on the reference value with standard deviation no greater than 64% of the mean.

Methods of the invention are based in part, on primary constraints that are imposed by the measurement modality. Information on certain constraints on realistic binding measurements are provided.

Binder Shot Noise

Although for the purposes of analysis, it has been assumed that all binders within 100 nm of the surface emit photons at an equal rate, while more distant binders emit no photons at all. It is also assumed that all emitted photons are collected. In reality, excitation due to higher-order beams that do not reflect at the interface will lead to some diffuse background from the bulk solution, and not all photons will be collected due to finite efficiencies in the optical path and at the detector, but contributions from these factors will depend significantly on the specifics of the optical setup. Some of these factors were accounted for in the simulations described herein below by calibrating with published DNA PAINT experiments. The term "observation field" is used to refer to the region occupied by fluorescent NAABs binding to a single, well-isolated, surface-anchored peptide. For the sake of simplicity, it is assumed that the observation field is imaged onto a single pixel on the camera, and assumed to constitute a cylindrical region 300 nm in diameter and 100 nm in depth, which are values that correspond to visible TIRF illumination.

To be able to distinguish the bound state from the unbound state, the number of photons emitted over the period of observation in the bound state must be significantly larger than the number of photons emitted in the unbound state. It is denoted by $\tau_{obs}$ the observation period (which may extend over multiple camera frames), by R the rate at which fluorophores in the observation field emit photons, and by $n_{free}$ the number of free binders in the observation field, which are referred to herein as the "occupation number" for brevity. The occupation number may be given in terms of the volume V of the observation field and the molecular number density of the binders $\rho$ by:

$$n_{free} = \rho V = 1000 N_A c V, \quad (2)$$

where c is the molar concentration and $N_A$ is Avogadro's number. There are two regimes that were of interest corresponding to $n_{free} \gg 1$ and $n_{free} \leq 1$. The choice of $n_{free}$ may be made by one skilled in the art and may be selected differently for different NAABs. It has been optimized to maximize the dynamic range of the $k_D$ readout experiment.

If $n_{free} \gg 1$, the number of photons emitted by the wee fluorophores in the observation field during the observation period are drawn from a Poisson distribution with mean and variance:

$$\lambda_f = R\tau_{obs} n_{free}. \quad (3)$$

On the other hand, in the bound state, the mean number of photons emitted is $$\lambda_b = R\tau_{obs}(n_{free}+1). \quad (4)$$

Then one can derive the requirement that:

$$R\tau_{obs} \geq 36(1+n_{free}) \quad (5)$$

The photon rate R is associated with the illumination intensity by $$R = \frac{I\epsilon}{1000 N_A h\nu}, \quad (6)$$

where $\epsilon$ is the molar absorptivity. A derivation for which is provided elsewhere herein. The minimum intensity that can be used is thus set by the constraints on R in equation (5). The following was obtained:

$$I \gg \frac{1000 N_A h\nu}{\epsilon} \frac{36(1+n_{free})}{\tau_{obs}}. \quad (7)$$

It is worth bearing in mind that an occupation number of $n_{free} \approx 1$ in every cylinder with diameter 300 nm and height 100 nm corresponds to a molar density of 235 nm.

In the case of $n_{free} \leq 1$, the noise may deviate significantly from a Poisson distribution as is described elsewhere herein. In this regime, it is likely easy to distinguish the bound and unbound states, and instead the constraints on R and $\tau_{obs}$ are set by the requirement that $R\tau_{obs}$ be greater than the read and dark noises of the camera. Modern sCMOS cameras have very low dark noises of 0.1 e⁻ per second, and read noises of only 1 to 2 e⁻ on average. The per-frame noise was denoted by p, measured in electrons, and by f the camera frame rate. Note that $\tau_{obs}$ may be determined independently of f, because the photon counts from multiple frames may be averaged in order to extend the observation period. Instead, f is constrained by practical considerations such as the per-frame read noise and the saturation point of the sensor. The following is used to overcome the read and dark noises:

$$R \gg pf. \quad (8)$$

The minimum intensity can thus be determined by the constraint:

$$I \gg \frac{1000 pf N_A h\nu}{\epsilon}. \quad (9)$$

A detector noise of p=1 electron per frame is now standard. To satisfy the requirement in equation (8) for the further calculations, it was taken as a requirement that in the limit of $n_{free} \leq 1$, should result in:

$$R\tau_{obs} \geq 9. \quad (10)$$

Photobleaching

The upper bound on the tolerable intensity was placed by photobleaching. Assuming continuous imaging, the fluorophore should remain active for the entire duration during which the fluorophore is bound. $N_q$ was used to denote the average number of photons that a fluorophore emits before it bleaches. There must be:

$$R/k_{off} \ll N_q. \quad (11)$$

In terms of the intensity, $$I \ll \frac{1000 N_A h\nu k_{off} N_q}{\epsilon}. \quad (12)$$

For a typical dye, such as ATTO647N, values of $N_q$ on the order of $10^7$ and $\epsilon \sim 1.5 \times 10^7$ M⁻¹ m⁻¹ have been reported [Jungmann R, et al., Nano letters. 2010; 10(11):4756-4761].

Stochastic Binding

Due to the stochastic nature of binding events, the length of the experiment must be chosen to be much longer than the average time between binding events. Hence, $$\frac{1}{k_{on}c} \ll \tau_{exp}, \quad (13)$$

where c is the concentration of free binders in the solution.

Methods of Data Analysis

Figures 2A, 2B:
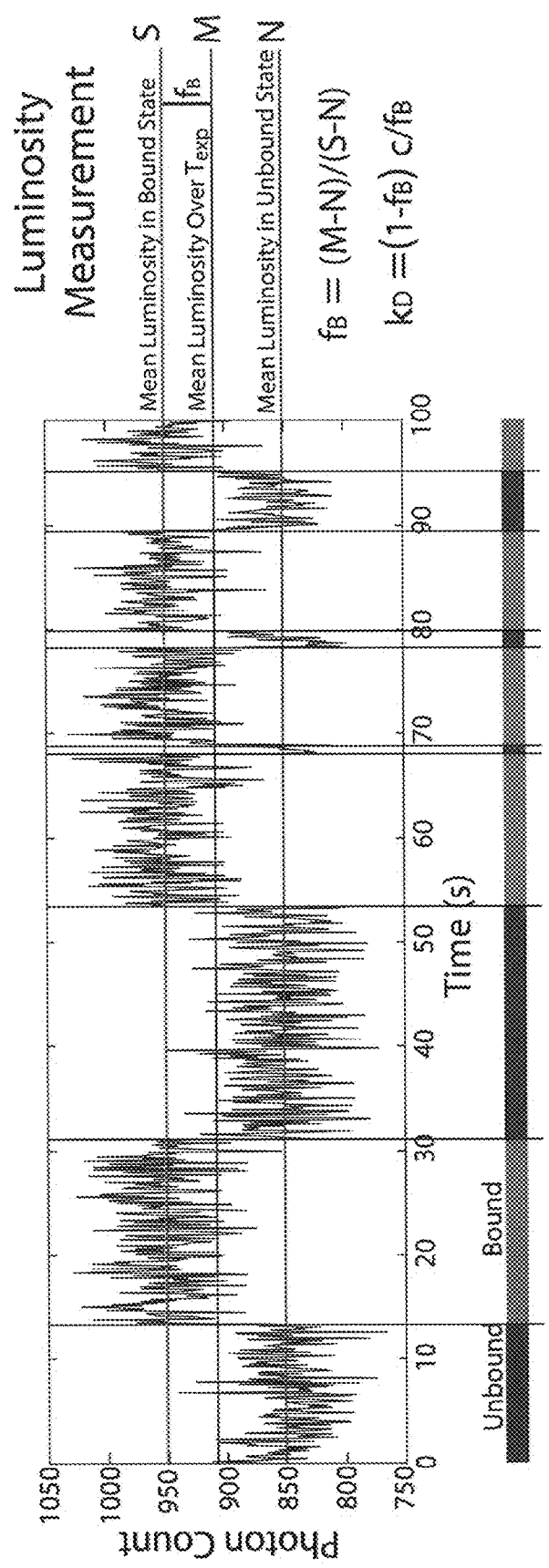
FIG. 2A-D provides a trace and graphs illustrating two types of affinity measures using TIRF microscopy.

A measurement performed using this scheme yields a time series such as that shown in FIG. 2A. The following are the two primary options for extracting the kinetics from the binding data and experimental conditions that are optimal for each scheme, given the constraints described above herein.

Occupancy Measurements

Figure 2C:
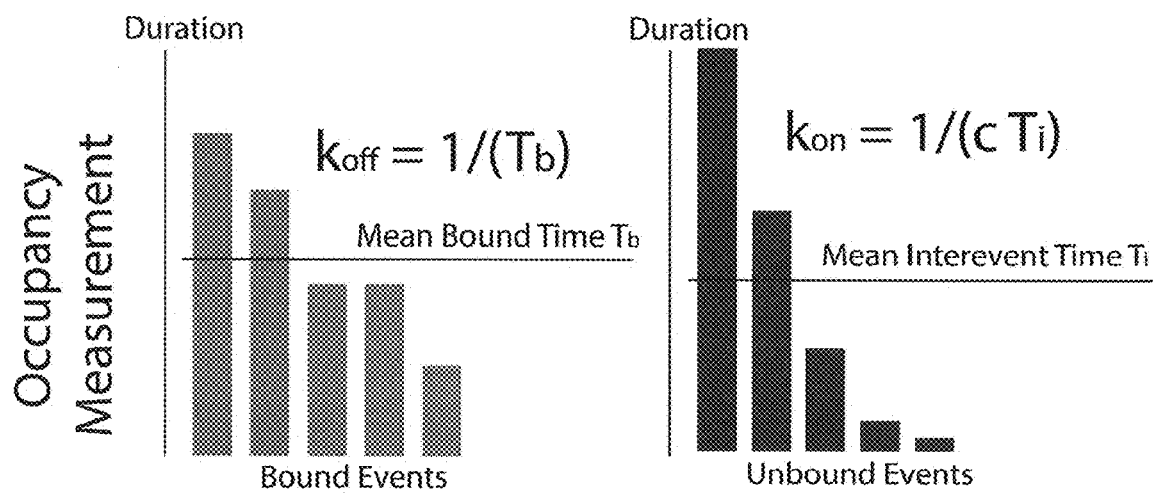
Figure 2D:
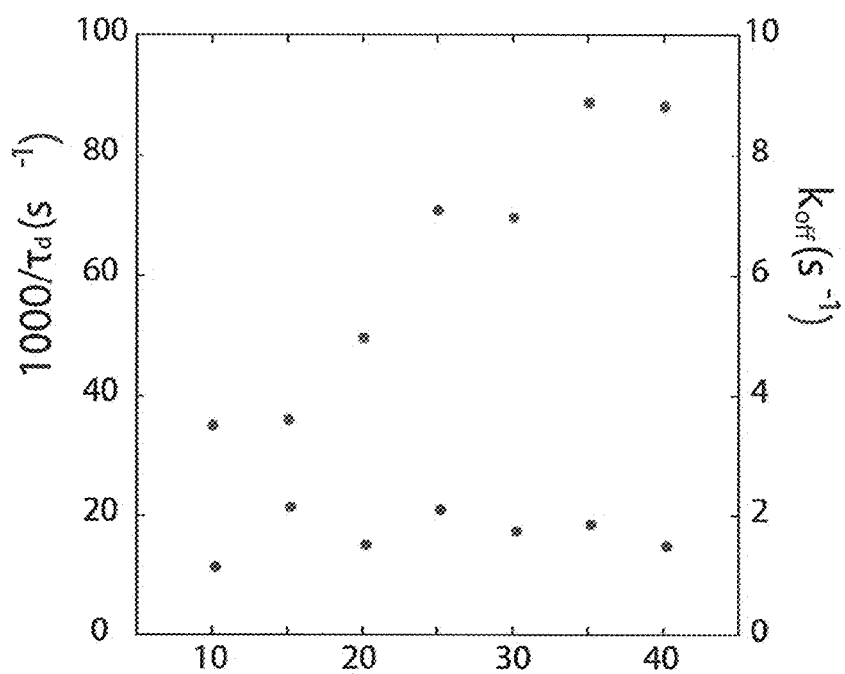

A first type of measurement that can be used in embodiments of methods of the invention, has been used in the field of single-molecule kinetics [Jungmann R, et al., Nano letters. 2010; 10(11):4756-4761 and van Oijen A M. Current Opinion in Biotechnology. 2011; 22(1):75-80], and relies on detecting changes in the occupancy state of the target. This measurement strategy is depicted schematically in FIG. 2C. FIG. 2D shows validation of the simulation by applying occupancy measurements to determine $k_{on}$ and $k_{on}$ from simulated data. The measurement is performed "along the time axis," in the sense that it relies on temporal information and relies on when probes bind and unbind. This method is relatively insensitive to analog luminosity information beyond that needed to make these digital determinations. This method is optimal for measurements on binders with very high affinities, which can be used at low concentrations. The upper limit on the dynamic range of this method is set by the frame rate, i.e.:

$$k_{off} \ll f, \quad (14)$$

where f is the imaging rate. In order to extract temporal information, the following is set: $\tau_{obs}=1/f$. This method will typically operate in the limit $n_{free} \leq 1$, so from equation (10), it is identified that there must be: $\tau_{obs} \geq 9$. Hence:

$$R/f \geq 9. \quad (15)$$

and hence:

$$R/9 \gg k_{off}. \quad (16)$$

On the other hand, the lower bound on the dynamic range is provided by photobleaching, as captured in equation (11). In total:

$$R/N_q \ll k_{off} \ll R/9. \quad (17)$$

In practice, for this measurement modality, the following was chosen: f=100 Hz and R=$10^4$ s$^{-1}$, corresponding to a laser power of 13 Wcm$^{-2}$. With $N_q$~$10^7$, the requirement becomes $k_{off} \ll 100$ s$^{-1}$ and $\tau_{obs} \gg 10^{-3}$ s$^{-1}$, yielding an effective dynamic range of approximately three orders of magnitude of $k_{off}$.

The experiment time is constrained by the requirement that $$T_{exp} \gg 1/(k_{on}c). \quad (18)$$

For a value of $k_{on}$ on the order of $10^5$ m$^{-1}$ s$^{-1}$ and a concentration on the order of 100 nm, this requirement implies that an experiment time of at least 100 seconds is necessary in order to see several binding events with high probability.

If the binding and unbinding events may be identified, then one may determine the average binding time $T_b$ and the average time between binding events $T_i$, which are referred to herein as the inter-event time. If photobleaching may be neglected, then the practitioner has:

$$k_{off} = \frac{1}{T_b}, \quad (19)$$

and $$k_{on} = \frac{1}{T_i c}, \quad (20)$$

where c is the free binder concentration. Thus, $$k_D = \frac{T_i}{T_b} c. \quad (21)$$

Alternatively, if the on-rate $k_{on}$ is known, then it is possible to determine $k_{off}$ even in the presence of photobleaching (see elsewhere herein for additional details).

Luminosity Measurements

An alternative to the occupancy-time measurements described above involves deducing $k_D$ directly from the fraction $f_B$ of time that the target is bound by a binding agent or probe. This quantity may in turn be deduced from the average luminosity of the spot containing the free binder over the period of observation, as depicted in FIG. 2B. Whereas occupancy measurements are performed "along the time axis," neglecting luminosity information, luminosity measurements are performed "along the luminosity axis," neglecting temporal information about the series of binding and unbinding events. Because it does not attempt to track individual binding and unbinding events, this method is particularly suited to measurements of weak binders performed at high background concentrations, where binding and unbinding events may occur faster than the camera frame rate. Moreover, this method of the invention relies on each NAAB of a given type having approximately the same brightness, which could be achieved using a high-efficiency method for monovalently labeling the NAAB N- or C-terminus [Nemoto N., et al., FEBS letters. 1999; 462(1):43-46 and Xu G, et al., ACS Chemical Biology. 2011; 6(10):1015-1020]. If a target is bound a fraction $f_B$ of the time, then the dissociation constant is given by:

$$k_D = \frac{1-f_B}{f_B} c, \quad (22)$$

where c is the background binder concentration. The average brightness of the spot when a fluorescent binder is attached to the target is denoted by S, and the average brightness of the spot when the target is free is denoted by N. Neglecting photobleaching, the average brightness of the spot over the whole experiment is given by $$M = f_B S + (1-f_B) N. \quad (23)$$

If S and N are known, then $f_B$ may thus be deduced directly from the measured photon rate M averaged over the entire experiment, via $$f_B = \frac{M-N}{S-N}. \quad (24)$$

S and N can be measured directly for example by anchoring NAABs sparsely to a surface and measuring the brightness of the resulting puncta (to deduce S), or puncta-free regions (to measure N).

One significant advantage of this method is that the observation period $\tau_{obs}$ can be chosen to be arbitrarily long by averaging the photon counts of many successive frames (i.e., $\tau_{obs}=T_{exp}$). In some embodiments of the invention, $\tau_{obs}=100$ s is used. With this value, a relatively high concentration of 2 μm (corresponding to $n_{free} \gg 1$) can be used even for a relatively low intensity of 1:3 Wcm$^{-2}$ (corresponding to R=$10^3$ s$^{-1}$, while still satisfying (Equation 5). Operating in this regime significantly reduces the vulnerability of the experiment to stochasticity and photobleaching. However, unlike in the case of occupancy measurements, there is no way to account for photobleaching, if it occurs. Nonetheless, it is not believed that photobleaching will have a significant impact on the results, because most of the NAABs have fairly high off-rates [U.S. Pat. No. 9,435,810 and Borgo B. & Havranek J J. Protein Science. 2014; 23(3):312-320].

In contrast to occupancy measurements, luminosity measurements are also sensitive to error in the calibration of the measurement apparatus, for example if the brightness of the bright and dark states is not known exactly. The bright and dark states S and N can be calibrated by doping in labeled reference peptides to the sample to be sequenced. Still, there may be some error in the measurements of S and N. A discussion of computational strategies for coping with calibration error is provided elsewhere herein.

Simulations

Simulation Studies

In order to determine whether the TIRF measurement scheme described above can be used to identify single amino acids on the N-termini of surface-anchored peptides, simulations of N-terminal amino acid identification experiments were performed.

Figure 5:
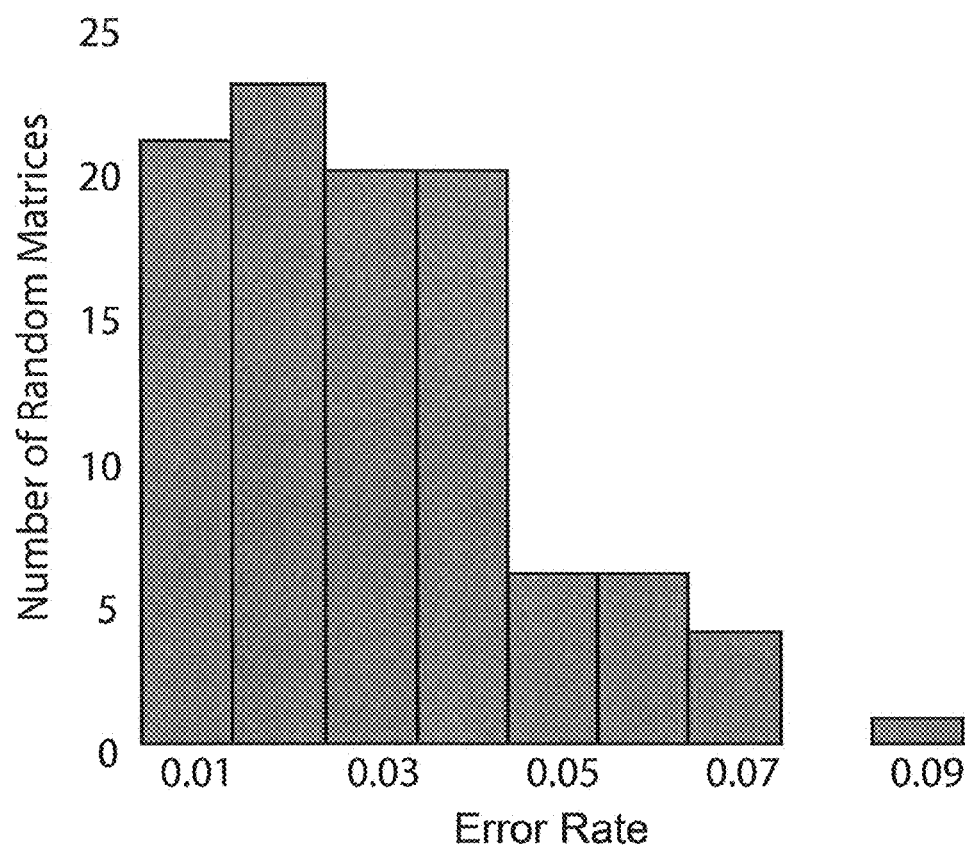
FIG. 5 provides a bar graph showing overall error rates for 100 random affinity matrices. The overall error rate, calculated as the sum of incorrect residue calls divided by the total number of residue calls over 10,000 trials, is plotted for 100 random affinity matrices.
Figure 6:
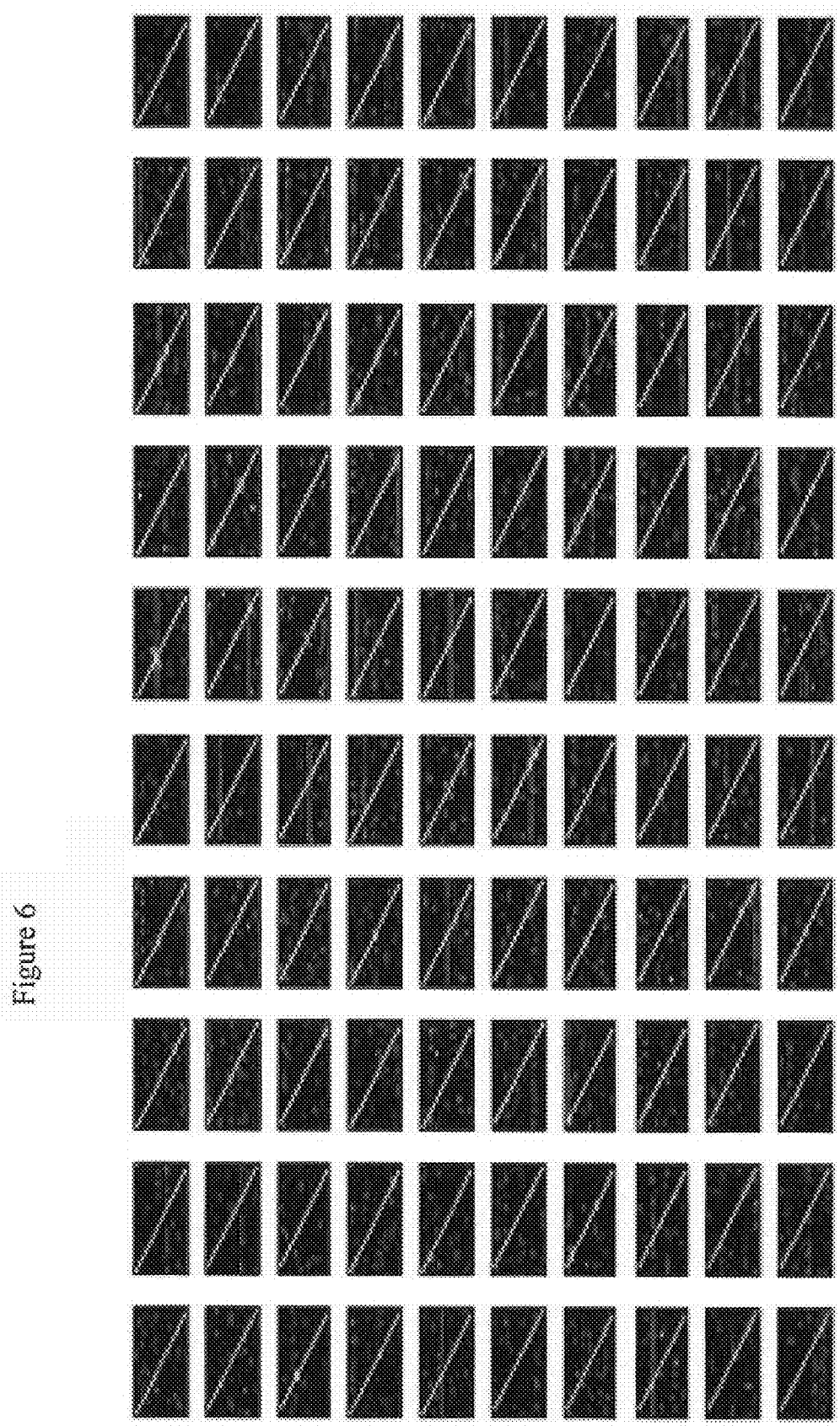
FIG. 6 shows affinity matrices and illustrates accuracies for amino acid calling obtained for 100 random affinity matrices in simulations. 100 random affinity matrices were generated by randomly shuffling the entries of the NAAB affinity matrix. For each resulting matrix, 10,000 amino acid calls were simulated, with 5% calibration error and 0.25% kinetic error. The resulting accuracy matrices are presented. The scale and axes for each matrix are identical to those in FIG. 4E.

First studies used a specific NAAB affinity matrix given in [U.S. Pat. No. 9,435,810]. Importantly, random affinity matrices generated by permuting the values of the NAAB affinity matrix perform similarly well in residue-calling simulations (FIGS. 5 and 6). To generate the random affinity matrices with statistics matching the statistics of the NAAB affinity matrix, each matrix element was chosen by randomly sampling values from the NAAB affinity matrix of [U.S. Pat. No. 9,435,810], without replacement. The simulations described here can therefore be assumed to apply to general ensembles of N-terminal binders with affinity value statistics similar to those displayed by these existing NAABs.

In the simulations, there was assumed to be one free target in the volume analyzed, which is a cylinder of diameter 300 nm and height 100 nm as described above herein. The simulation considers each frame of the camera in succession, and models the number of photons registered at the camera. At the start of the simulation, or as soon as the target becomes free, a time $T_{free}$ is drawn from an exponential distribution with mean $1/(k_{on}c)$, where c is the concentration of binders. Once a time equal to $T_{free}$ has passed, the binder was considered occupied, and a time $T_{bound}$ was drawn from an exponential distribution with mean $1/k_{off}$. In addition, upon binding, a time $T_{photobleach}$ was drawn from an exponential distribution with mean $N_q/R$, where $N_q$ is the number of photons the fluorophore emits on average before bleaching and R is the single-fluorophore photon rate. If the time $T_{photobleach}$ is less than the time $T_{bound}$, the fluorophore ceases to emit photons after time $T_{photobleach}$. Within a given frame, the simulation tracked binding, unbinding, and photobleaching events, and computed the number of signal photons detected by the camera by drawing from a Poisson distribution with mean $RT_{on}$, where R is the single fluorophore photon rate and $T_{on}$ is the amount of time during the frame in which an unbleached fluorophore was attached to the target.

The dominant contribution to noise in the simulation is expected to come from fluorophores attached to free binders that enter and leave the observation field [van Oijen A M. Current Opinion in Biotechnology. 2011; 22(1):75-80]. At the end of each frame, the simulation draws the number of free binders that enter the observation field during the frame from a Poisson distribution with mean $n_{free}/f$, where f is the frame rate and $n_{free}$ is the free binder occupation number of the frame. For each binder that enters the observation field, a dwell time t was drawn from an exponential distribution with mean $\tau_{dwell}$ as calculated in equation (40) from diffusion theory (additional detail elsewhere herein), and a total photon contribution from a Poisson distribution with mean Rt. Finally, steps were performed to calculate the detector shot noise from a Gaussian distribution with mean p and standard deviation equal to 0:1p.

Validation of the Simulation Pipeline

To validate the simulations, the DNA PAINT kinetics data collected by [Jungmann R, et al., Nano letters. 2010; 10(11): 4756-4761] were reproduced using the parameters reported in that publication. There, values of $k_{on}=10^6$ m$^{-1}$ s$^{-1}$ and $k_{off}=2$ s$^{-1}$ were reported. Imaging was conducted at 650 nm with a power of 4 mW to 8 mW over an imaging region of (150 μm)$^2$, corresponding to an intensity of approximately 26:67 W cm$^{-2}$, corresponding to a photon rate of R~18 000 s$^{-1}$, assuming a dye comparable to ATTO655. However, accounting for the low quantum efficiency of ATTO655 and possible losses of light in the light path of the microscope, the simulations were performed with R~1500 s$^{-1}$. From the simulated data, the measured off- and on-rates were able to be reproduced, as shown in FIG. 2D. Moreover, consistent with [Jungmann R, et al., Nano letters. 2010; 10(11):4756-4761], photobleaching only became apparent in the simulation at laser powers greater than 100 mW.

Measurements of $k_D$

Occupancy Measurements

Next, studies were performed to simulate occupancy measurements of the binding kinetics of the NAAB against the target. One hundred simulations were performed for each of five different values of $k_{on}$ between $10^4$ m$^{-1}$ s$^{-1}$ and $10^6$ m$^{-1}$ s$^{-1}$, which is consistent with standard values observed for antibodies [Foote J. & Eisen H N. PNAS (USA). 1995; 92(5):1254], and for each of five different values of $k_D$ between 100 μm and 10 nm. Studies assumed a framerate of 100 Hz, detector read noise of 1 e$^-$, and a laser power of 130 kWm$^{-2}$, corresponding to a single-fluorophore photon rate of $10^4$ s$^{-1}$. NAABs were washed onto the sample at a concentration of 300 nm, and each wash was observed for $T_{exp}=100$ s.

In order to analyze the data, a control simulation was run in which $k_{on}$ was set to 0, so that no NAABs bound to the target. In practice, this calibration can also be performed by observing a spot that does not have a target. From this, the mean and standard deviation of the noise on a per-frame basis were calculated. Next binding and unbinding events were identified as follows. First, all frames in which the photon count was more than 2 standard deviations above the noise mean were identified. These frames were referred to as "on" frames, whereas all other frames were referred to as "off" frames. If three such "on" frames occurred in a row, the event was identified as a binding event. The binding event was considered to continue until at least two "off"-frames in a row were observed. Once all the binding and unbinding events were identified, the average inter-event time and the average binding time were calculated, and from these the kinetics were determined (FIG. 2A).

Figure 3A:
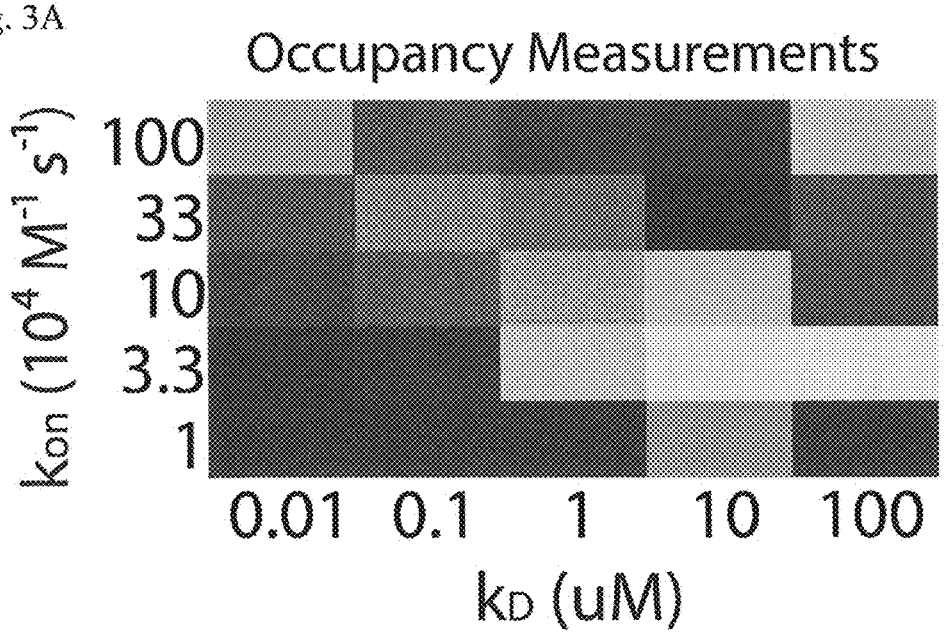
FIG. 3A-D provides heat maps and graphs illustrating two types of affinity measurements using TIRF microscopy.

The accuracy of the $k_D$ measurements was found to improve with increasing $k_{on}$, and to improve with increasing $k_D$ for values of $k_{off}$ below 10 s$^{-1}$ (FIG. 3A). For values of $k_{off}$ significantly above 10 s$^{-1}$, it was no longer possible to distinguish individual binding and unbinding events from noise (FIG. 3A, upper right-hand corner). Moreover, for values of $k_{on}$ below 10$^5$ m$^{-1}$ s$^{-1}$, the condition $T_{exp} \gg 1/(k_{on}c)$ was no longer satisfied. Finally, for very small values of $k_D$, photobleaching limited the accuracy of the analysis. For $k_{on} > 10^5$ m$^{-1}$ s$^{-1}$ and $k_{off} \sim 10$ s$^{-1}$, it was possible to obtain the correct value of $k_D$ to within approximately 5-10%. However, the accuracy deteriorated sharply for combinations of $k_{on}$ and $k_{off}$ deviating from these ideal conditions.

Luminosity Measurements

Studies were then performed simulating luminosity measurements of $k_D$ using comparable parameters. Because these measurements depend only on the average luminosity over the entire experiment, the entire experiment was lumped into a single camera frame. In practice, however, the same results can be obtained by averaging over the photon counts of multiple frames. The laser intensity was set to 13 kW m$^{-2}$, corresponding to a single-fluorophore photon rate of R=1000 s$^{-1}$, and the free binder concentration was set to 2 μm. The photon rate of the off-state was determined first by running the simulation with the value of $k_{off}$ set to 0. The photon rate in the on-state was then determined by running the simulation with the value of $k_{on}$ set to 10$^{10}$ m$^{-1}$ s$^{-1}$, and the value of $k_D$ set to 10$^{-20}$ M. Because the exposure time used in this experiment was very long compared to the dwell time of free binders in the observation field, it was assumed that all free binders that enter the observation field emit a number of photons equal to $R\tau_{dwell}$ (i.e., the noise was taken to be approximately Poissonian), which substantially reduced the computational complexity of the algorithm. Once the average luminosity over the experiment was determined, the value of $f_B$ was deduced.

For observation times shorter than 50 s, the analysis sometimes returns values of $f_B$ arbitrarily close to or greater than 1 or arbitrarily close to or less than 0. This can happen as a consequence of statistical error in the luminosity measurements, even in the absence of systematic error. For this reason, in order to avoid negative or outlandishly large values of $k_D$ from compromising the analysis, the maximum value of $f_B$ was chosen to be equal to the value expected when $k_D$=1 nm, and the minimum value of $f_B$ was chosen to be equal to the value obtained when $k_D$=10 mm. Any values of $f_B$ outside of this range were adjusted to the maximum or minimum value, appropriately.

Figure 3B:
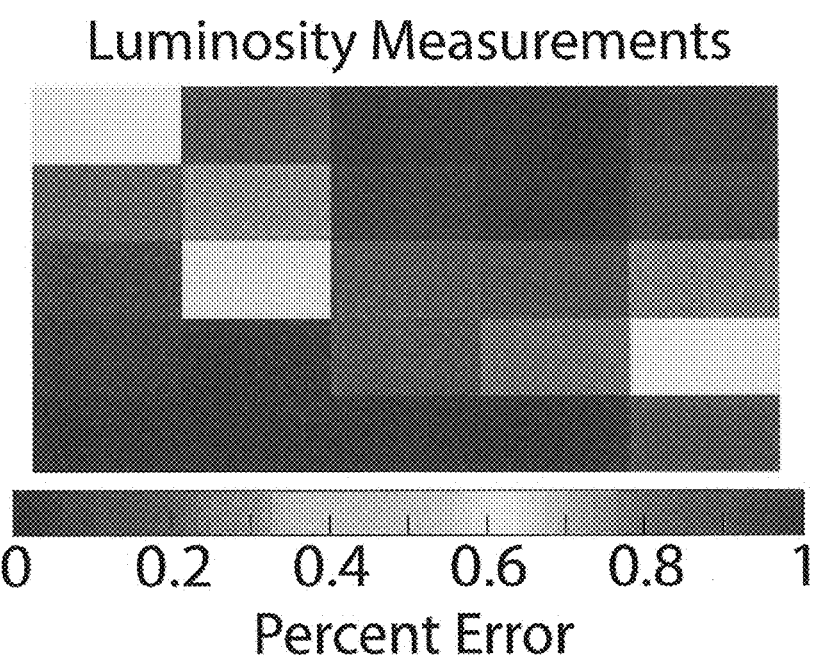

In order to enable comparison to the occupancy measurements, the simulation was run 100 times for each of five values of $k_{on}$ between 10$^4$ m$^{-1}$ s$^{-1}$ and 10$^6$ m$^{-1}$ s$^{-1}$ and for each of five values of $k_D$ between 100 μm and 10 nm. The accuracy was found to be comparable to that obtained in the occupancy experiments (FIG. 3A), except that the accuracy did not deteriorate for very high values of $k_{off}$ (FIG. 3B, upper right-hand 3 corner). For values of $k_{on}$ on the order of (or greater than) 10$^5$ m$^{-1}$ s$^{-1}$ and values of $k_D$ greater than 1 μm, $k_D$ could easily be determined to within the accuracy condition required by equation (31).

Figure 3C:
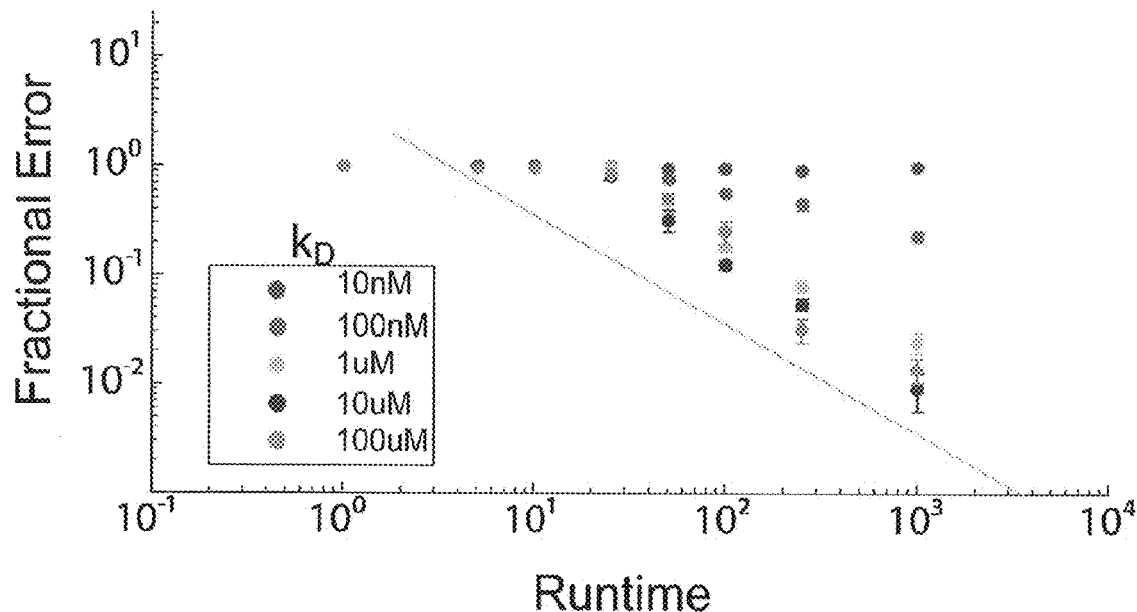
Figure 3D:
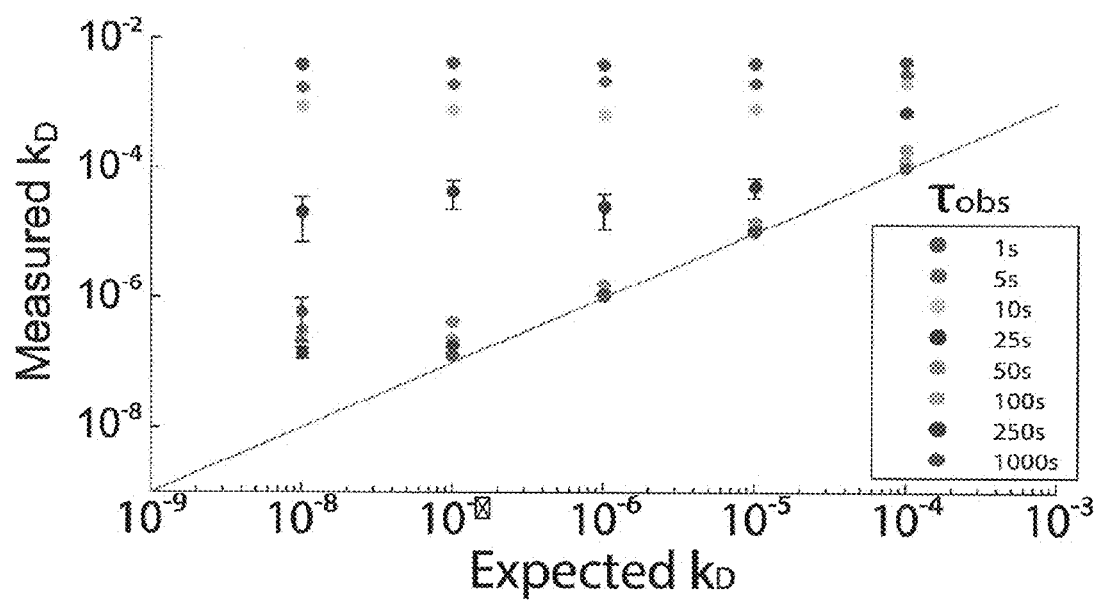

To ascertain the effect of $\tau_{obs}$ on the accuracy, the simulation was run 100 times for each of the same 25 combinations of $k_{on}$ and $k_{off}$ with 8 different values of $\tau_{obs}$ between 1 s and 1000 s and a free binder population of 2 μm (FIG. 3C). As expected, the accuracy was found to undergo a sharp transition when $\tau_{obs}$ was on the order of 25 s, corresponding to $1/(k_{on}c) \ll \tau_{obs}$. For values of $\tau_{obs} > 25$ s and values of $k_D$ greater than 1 μm, the error in the measurement of $k_D$ decreased like $1/\tau_{obs}$ (FIG. 3C). For observation times greater than 25 s, the value of $k_D$ could be calculated with standard deviation less than 64% of the mean for values of $k_D$ on the order of or greater than 1 μm, although photobleaching led to saturation and significant losses of accuracy for smaller values of $k_D$ (FIG. 3D).

Separately, to ascertain the effect of the free binder concentration on the accuracy, the simulation was run 1000 times on each of the same 25 combinations of $k_{on}$ and $k_D$, with $\tau_{obs}$=50 s at seven different values of the concentration between 10 nm and 5 μm. For values of $k_{on}$ such that $\tau_{obs} \gg 1/(k_{on}c)$, the effect of increasing $k_{on}$ was found to be similar to the effect of increasing $\tau_{obs}$ (data not shown).

Identifying Amino Acids

Because standard deviations in $k_D$ below 64% of the mean could consistently be achieved in the luminosity measurements across a broad range of values of $k_{on}$ and $k_D$, it was reasonable to expect that luminosity measurements of NAAB binding kinetics could allow for the identification of amino acids at the single molecule level. A simulation experiment was performed in which a peptide with an unknown amino acid was attached to a surface, and was observed successively in multiple baths, each containing a single kind of fluorescent NAAB. In this simulation, amino acids were randomly chosen from a uniform distribution. Binders were added to the solution at a concentration of 1 μm and the laser power was set to 13 kW m$^{-2}$. For each NAAB, effective values of the dissociation constant $\tilde{k}_D$ the on-rate $\tilde{k}_{on}$, the effective brightness $\tilde{R}$, and the calibration levels $\tilde{S}$ and $\tilde{N}$ were determined for the NAAB-amino acid pair. The spot containing the NAAB was then observed over a period of time $\tau_{obs}$, which ranged from 50 to 500 seconds, and the total number of photons observed was stored. This process was repeated for each NAAB, generating a vector $\vec{M}$ of observed photon counts. Systematic error in the experiment was parametrized using three quantities. For each NAAB, the effective dissociation constant $k_D$ for the NAAB-amino acid pair was drawn from a normal distribution centered on the reference value $k_D$, with standard deviation equal to $\sigma_K k_D$, where $\sigma_K$ parametrizes the effect of non-terminal amino acids and other environmental factors on the dissociation constant. Likewise, the effective brightness of the NAAB relative to the average NAAB brightness was determined by drawing $\tilde{R}$ from a normal distribution with mean R and standard deviation $\sigma_B R$, where R is the photon rate of a standard fluorophore (assumed here to be ATTO647N) in the observation field. Finally, in order to determine the effective calibration levels, the true calibration levels S and N were first determined as the luminosity of the bound and unbound states, as described above herein (Luminosity Measurements). The measured calibration levels $\tilde{S}$ and $\tilde{N}$ were then determined by drawing from a normal distribution with mean equal to S and N and with standard deviation equal to $\sigma_C S$ and $\sigma_C N$, respectively. The values of $\sigma_K$, $\sigma_B$, and $\sigma_C$ are provided below in percentages.

Analysis was performed by comparing the measured photon counts to the photon counts that would have been expected for each amino acid, as described above herein. For each NAAB-amino acid pair, the expected photon count was calculated from the NAAB concentration c, the reference value of $k_D$ and the measured calibration level $\tilde{S}$ and $\tilde{N}$, via $$\vec{E} = \frac{c}{c+k_D}\tilde{S} + \left(1 - \frac{c}{c+k_D}\right)\tilde{N}. \quad (25)$$

The resulting expected photon counts were then assembled into a matrix W, such that the (i,j)th element of W was the photon count that would be expected on the measurement of the ith NAAB if the target were the jth amino acid, given the calibration levels $\tilde{S}$ and $\tilde{N}$. Finally, the amino acid identity $I_{aa}$ was determined by minimizing the norm between the vector of observed photon counts $\vec{M}$ and the columns of W, i.e.:

$$I_{aa} = \mathrm{argmin}_k \|\vec{M} - \vec{w}_k\|, \quad (26)$$

where $\vec{w}_k$ is the kth column of W.

Figure 4E:
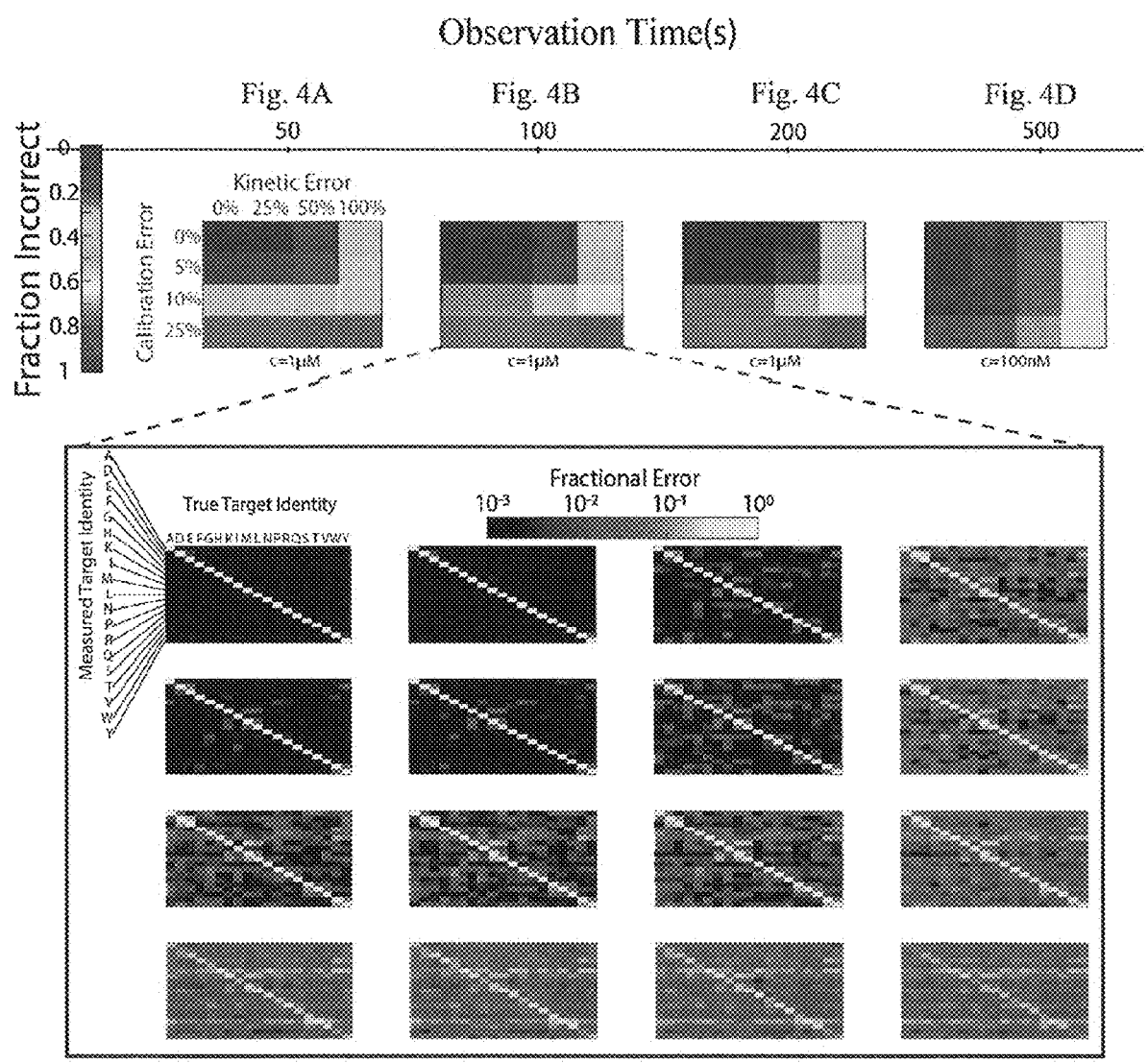
FIG. 4E illustrates that for $\tau_{obs}=100$ s, plots are shown for each value of $\sigma_C$ and $\sigma_K$, depicting the probability that a given target amino acid (on the horizontal axis) was assigned a particular identity (on the vertical axis). Off-diagonal elements correspond to errors.

In FIG. 4A-C, the accuracy with which amino acids can be identified is shown as a function of the observation time and the systematic error, for a 1 μm free binder concentration. In the absence of systematic error, amino acids could be identified with greater than 99% accuracy after a 50 s observation. Moreover, if the calibration error could be kept below 5%, and if the systematic error in the kinetics could be kept below 25%, then the simulations indicated that it would be possible to identify amino acids with greater than 97.5% accuracy over an observation window of 100 s.

The measurement accuracy was shown to be robust against systematic differences in brightness between different NAABs (data not shown). The experiment also showed robustness against systematic deviation in $k_D$ up to the 25% level, with progressive deterioration in the measurement accuracy observed for values of $\sigma_K$ above 25%. Calibration error was found to have the most substantial effect on the accuracy, with calibration errors on the order of 10% reducing the achievable accuracy below 90% even for an observation time of 250 s. The effects of calibration error on the accuracy could be substantially reduced by reducing the concentration of free binders (FIG. 4D), which has the effect of increasing the gap between the S and N. However, in order to preserve the requirement that $T_{exp} \gg 1/(k_{on} c)$, it was necessary to increase the experiment length by a similar factor. (It is worth noting that for this reason, a free NAAB concentration of 1 μm was used, rather than 2 μm as used above.) Moreover, this improvement resulted in increased sensitivity to systematic error in $k_D$.

Application to Randomized Affinity Matrices

In order to determine whether the protein sequencing method of the invention was limited to the specific affinity matrix given in [U.S. Pat. No. 9,435,810], affinity matrices were generated with comparable binding statistics by randomly shuffling the $k_D$ values in the NAAB affinity matrix. For 100 such random affinity matrices, identical simulations as in FIG. 4E, were performed, assuming 5% calibration error and 25% kinetic error. To calculate the overall error rate for a given matrix, the frequencies of incorrect residue calls (the off-diagonal elements of the matrices in FIG. 4E) were summed. The overall error rate for the NAAB affinity matrix, calculated in this way, was 0.0124, and the distribution of error rates across the random matrices is shown in FIG. 5. Only one randomly generated affinity matrix had an error rate lower than the NAAB error rate. Nonetheless, it was clear that most affinity matrices with affinity statistics similar to the NAABs [U.S. Pat. No. 9,435,810] would yield errors in the range of 1%-4%, and thus the sequencing method of the invention as described herein is generalizable to a range of similar N-terminal amino acid binders.

The calculations and simulations discussed herein indicated that if the measurement apparatus can be calibrated with an accuracy of 5%, and if the reference values of $k_D$ can be kept within 25% of the true values, it is theoretically possible to determine the identity of an N-terminal amino acid with greater than 97.5% accuracy by measuring the kinetics of the NAABs against the target amino acid. Crucially, $k_D$ can be inferred just from the time-averaged local concentration of NAABs within the observation field, and thus the measurement can be performed at relatively high background binder concentrations, because it does not rely on being able to distinguish individual binding and unbinding events.

Discussion

Three primary uncertainties exist regarding the validity of the simulations performed here. Firstly, the simulation did not incorporate the effects of non-specific binding of NAABs to the surface. Nonetheless, if such non-specific binding occurs with sufficiently low affinity, it is expected that the effect of the non-specific binding will be comparable to the effect of increasing the affinity of the binders for the target, and it has now been shown that the experiment displays considerable robustness against such sources of systematic error. On the other hand, if non-specific binding occurs with high affinity, it is expected that by examining the time-course of the luminosity, such non-specific binding events can be identified and accounted for. In addition, some uncertainty exists surrounding the value of $N_q$ for certain organic dyes of interest, with values between $10^5$ and $10^7$ being reported [Jungmann R, et al., Nano letters. 2010; 10(11):4756-4761 and Dempsey G T, et al., Nature Methods. 2011; 8(12):1027-1036]. However, it is expected that the method to be relatively robust to photobleaching due to the relatively low affinity and high off-rates of most of the NAABs. Moreover, it is possible that more photostable indicators such as quantum dots could be used in place of organic dyes. Note that with any labeling scheme, there will be some concentration of "dark NAABs" that are not labeled. Thus, the concentrations reported for the simulations above should be regarded as the concentrations of "bright NAABs." The presence of dark NAABs is unlikely to affect the experimental results provided the total NAAB concentration is less than the dissociation constant (i.e., as long as the target is free most of the time), so a high concentration of dark NAABs can always be compensated for by reducing the total NAAB concentration and increasing the measurement duration.

Parallelization

It is believed that the approaches discussed here can be parallelized in a way reminiscent of next-generation nucleic acid sequencing technologies, thus methods of the invention can be used in massively parallel protein sequencing with single-molecule resolution. In a non-limiting example, if a 64 megapixel camera were used with one target per pixel, it would result in the ability to observe the binding kinetics of NAABs against approximately $10^7$ protein fragments simultaneously. With an observation time of 100 seconds per amino acid-NAAB pair, this corresponds to approximately 35 minutes of observation time per amino acid, or 5 days to identify a protein fragment of 200 amino acids in length. On average, therefore, the sequencing method would have a throughput of approximately 20 proteins per second.

However, the throughput of the device can be improved dramatically if the readout mechanism are electrical, rather than optical. CMOS-compatible field-effect transistors have been developed as sensors for biological molecules [Cui Y, et al., Science. 2001; 293(5533):1289-1292 and Kim A, et al., Applied Physics Letters. 2007; 91(10):103901-103901]. Moreover, electrical sequencing of DNA has been accomplished using ion semiconductor sequencing [Rothberg J M, et al., Nature. 2011; 475(7356):348-352]. Most recently, CMOS-compatible carbon nanotube FETs have been shown to detect DNA hybridization kinetics with better than 10 ms time resolution [Bellin D L, et al., Biomedical Circuits and Systems Conference (BioCAS), 2014 IEEE. IEEE; 2014. p. 476-479 and Sorgenfrei S, et al., Nature Nanotechnology. 2011; 6(2):126-132]. Similar CMOS-compatible devices have been adapted to the detection of protein concentrations via immunodetection [Lu N, et al., ACS Applied Materials & Interfaces. 2014; 6(22):20378-20384]. These systems have the added benefit that they sense from a much smaller volume than TIRF does (sometimes as small as ~10 cubic nanometers [Sorgenfrei S, et al., Nature Nanotechnology. 2011; 6(2):126-132]), substantially reducing the impact of noise on the measurement. A single 5 inch silicon wafer covered in transistor sensors at a density of 16 transistors per square micron would be capable of sequencing 1012 proteins simultaneously, corresponding to an average throughput of 2,000,000 proteins per second on a single wafer, or one mammalian cell every 7 minutes. Such an approach can make use of dedicated integration circuitry to compute the average NAAB occupancy at the hardware level, greatly simplifying data acquisition and processing. Moreover, if the devices were made CMOS-compatible, they could be produced in bulk, greatly improving scalability. If the intrinsic contrast provided by the NAABs is insufficient for measurements with FETs, the NAABs can be further engineered to have greater electrical contrast, for example by conjugating them on the C-terminus to an electrically salient protein such as ferritin. A combination of electrical and optical readouts are also encompassed in certain embodiments of the invention. For example, certain methods of the invention may include use of art-know CMOS-compatible single-photon avalanche diode imaging systems that are capable of detecting the presence of fluorophores on a surface without magnification [Guo N, et al., Sensors. 2014; 14(10:20602-20619]. In some embodiments of the invention, in addition to or instead of using a TIRF microscope, detection may comprise use of electrical and/or optical sensors on a chip positioned right below the surface where the proteins are binding, wherein the electrical and/or optical sensors are used for detection, without a need for magnifying optics, and potentially with more confinement of the sensing volume compared to wide-field TIRF microscopy.

Although embodiments of the invention that include use of TIRF microscopy may restrict the method to operating close to a reflecting surface, other embodiments of methods of the invention include use of thin sections and/or alternative microscopies and permit protein sequencing methods of the invention to operate in-situ inside intact cells or tissues.

It has now been shown that single molecule protein sequencing is possible using low-affinity, low-specificity binding reagents and single molecule fluorescent detection. Certain embodiments of methods of the invention utilize high-quality single molecule surface chemistry and a TIRF measurement setup. Details and results provided herein indicate that a wide range of binding reagent families may be useful in single molecule protein sequencing.

Additional Information

Due to stochasticity, noise, and context-dependence (e.g. sequence-dependence) of the NAAB-amino acid interactions, a measurement performed on the kth target will yield an approximation $\vec{w}$ to the reference affinity vector $\vec{w}_k$. If it is assumed that the distribution according to which these measurements occur is Gaussian, a simple criterion can be obtained for determining whether two N terminal amino acids will be distinguishable on the basis of affinity measurements made using a particular set of NAABs. The standard deviation of the measurements made with NAAB i against amino acid j were denoted by: $\sigma_j^{(i)}$. For each amino acid, a sphere of radius $p_j$ may be defined, centered on the vector $\vec{v}_j$, which surrounds that amino acid in affinity space. Here, $$\rho_j = 3 \max_i \frac{\sigma_j^{(i)}}{K_j^{(i)}}, \tag{27}$$

where $K_j^{(i)}$ is the dissociation constant for the binding of the ith NAAB to the jth amino acid. N-terminal amino acids will be identifiable with 99.9% certainty provided that there is no overlap in affinity-space between the j spheres of radius $p_j$. To determine whether there is such an overlap, the following distance metric is considered:

$$D \equiv \min_{i, j \neq i} \left\| \frac{\vec{v}_i - \vec{v}_j}{\vec{v}_i} \right\|, \tag{28}$$

where the division is applied element-wise. In order to assign affinity measurements to the correct reference affinity 99.9% of the time, it is sufficient (but not necessary) to have $$\max_{i, j \neq i} (\rho_i + \rho_j) \leq D. \tag{29}$$

Using equation (27), it is then also sufficient to have:

$$6 \max_{i, k \neq i} \frac{\sigma_k^{(i)}}{K_k^{(i)}} \leq D. \tag{30}$$

For the specific case of the NAAB affinity matrix, it has been found that D=3:84. Thus, in order to ensure that the amino acids can be correctly identified 99.9% of the time, it is necessary to have $$\max_{i,k\neq i} \frac{\sigma_k^i}{K_k^{(i)}} \leq 0.64, \qquad (31)$$

or, equivalently, the standard deviation of the $k_D$ measurements must be no greater than 64% of the mean.

Under the assumption of Poissonian noise, the photon rates in the bound and unbound states are given by:

$$\lambda_f = R\tau_{obs} n_{free} \qquad (32)$$

and $$\lambda_b = R\tau_{obs}(n_{free}+1) \qquad (33)$$

respectively. In order to be able to distinguish the bound state from the unbound state, it is clear that there must be $$\lambda_f + 3\sqrt{\lambda_f} \leq \lambda_b - 3\sqrt{\lambda_b}. \qquad (34)$$

Because $\lambda_b > \lambda_f$, the standard deviation $\sqrt{\lambda_f}$ on the left-hand side may be replaced by the standard deviation $\sqrt{\lambda_b}$, obtaining:

$$\lambda_f \leq \lambda_b - 6\sqrt{\lambda_b}. \qquad (35)$$

Hence, $$R\tau_{obs} \geq 6\sqrt{R\tau_{obs}(n_{free}+1)}. \qquad (36)$$

And the final requirement is:

$$n_{free} \leq \frac{R\tau_{obs}}{36} - 1. \qquad (37)$$

Rephrased as a condition on the concentration of the binder, it is found:

$$c \leq \frac{\frac{R\tau_{obs}}{36} - 1}{1000 N_A V}, \qquad (38)$$

or $$R\tau_{obs} \geq 36(1+n_{free}). \qquad (39)$$

If $n_{free} \leq 1$, then the assumption of Poissonian noise is invalidated because the emission of successive photons is not independent (it depends on the presence of fluorophores in the observation field). The assumption of Poissonian noise may also be invalidated if the frame rate is comparable to the rate at which fluorophores enter and leave the observation field. In either case, to correctly simulate the noise, one must draw the number of free binders that enter the observation field during a given frame from a Poisson distribution with mean $n_{free}\tau_{obs}=\tau_{dwell}$, where $\tau_{dwell}$ is the amount of time each binder spends in the observation field on average. The average dwell time of free binders in a region of thickness $\Delta x$ may be calculated as:

$$\tau_{dwell} = (\Delta x)^2/D, \qquad (40)$$

where D is the diffusion constant [Edman P, et al. Acta Chem Scand. 1950; 4(7):283-293]. For a small protein in water, one has $D \sim 10^{-10}$ m$^2$ s$^{-1}$. Taking $\Delta x=100$ nm, it is found that free binders will dwell on average $\tau_{dwell}=100$ μs within the imaging plane.

Once the number of binders entering the observation field during the frame has been determined, one must draw the length of time t that each binder remains in the frame from an exponential distribution with mean $\tau_{dwell}$. Finally, for each binder, one must draw the number of photons emitted by that binder from a Poisson distribution with mean Rt. When the number of free binders is small, the resulting noise will differ significantly from Poisson noise due to the exponential distribution over dwell times. In the simulations, performed, the long tail of the exponential distribution tends to significantly increase the difficulty of distinguishing transient binding and unbinding events, compared to simple Poisson noise (data not shown).

The intensity I is related to the photon rate R of the fluorophore by:

$$I = R\frac{h\nu}{\sigma}, \qquad (41)$$

where h is Planck's constant, $\nu$ is the frequency, $\sigma$ is the absorption cross-section of the fluorescent dye, and R is the rate of absorption. To determine the cross-section, it was noted that from the Beer-Lambert law, $$\varepsilon c = \alpha, \qquad (42)$$

where $\alpha$ is the attenuation coefficient, c is the molar concentration, and $\varepsilon$ is the molar absorptivity, which is assumed to be given in M$^{-1}$ m$^{-1}$. Furthermore, one has $$\sigma = \alpha/n, \qquad (43)$$

where $\sigma$ is the absorption cross-section and n is the atomic number density. Hence, one has $$\sigma = \varepsilon c n, \qquad (44)$$

or, since c is the molar concentration and n is the number density, one has $n=1000\, N_A c$, where $N_A$ is Avogadro's constant, c is given in molar and n is given in atoms per cubic meter. Thus, $$\sigma = \frac{\varepsilon}{1000 N_A}. \qquad (45)$$

Hence, the photon number is given in terms of the intensity by $$R = \frac{I\varepsilon}{1000 N_A h\nu}. \qquad (46)$$

One advantage of occupancy measurements is that if $k_{on}$ is known, then $k_{off}$ may be determined even in the presence of photobleaching. To do so, it was noted that $T_i$ and $T_b$ are independent variables that depend on $k_{off}$, $k_{on}$, and $N_q$. In the above analysis, it was assumed that $N_q$ was infinite, so that quenching could be neglected. If $N_q$ is finite, however, then the true expressions for $T_i$ and $T_b$ are given by $$T_b = \frac{1}{k_{off} + R/N_q}, \qquad (47)$$

and $$T_i = \underbrace{\left(\frac{1}{k_{off}} - T_b\right)}_{\text{target occupied}} + \underbrace{\frac{1}{k_{on}c}}_{\text{target unoccupied}}. \qquad (48)$$

The first term in equation (48) is the average time the target spends occupied by a quenched fluorophore, while the second term is the average time the target spends unoccupied between unbinding and binding events. Hence, if $k_{on}$ is known, then $k_{off}$ and $N_q$ may be determined from $T_b$ and $T_t$.

In contrast to occupancy measurements, luminosity measurements are sensitive to error in the calibration of the measurement apparatus. Calibration error arises from a combination of systematic differences in the brightness of the on- and off-states, which may result if different NAABs have different numbers of fluorophores on average, and from systematic error in the measurement of the brightnesses of the on- and off-states. Systematic variation in the brightnesses of the fluorophores can be overcome by calibrating the device prior to each measurement (as discussed herein). In general, however, systematic error in the measurement of S and N significantly disrupts attempts to determine the absolute value of $k_D$ due to divergences in the derivative of $k_D$ as M approaches N. Hence, for weak binders in particular, infinitesimal changes in the calibration level can lead to divergent changes in the measured value of $k_D$. For this reason, if the goal of the measurement is to determine the absolute value of $k_D$, it is essential that the concentration be chosen such that the value of M to be measured lies close to S, i.e., such that the concentration c is close to or greater than $k_D$. If $k_D$ is large or unknown, however, this requirement may not be achievable.

In certain embodiments of the invention, in which a goal is not to determine the absolute value of $k_D$, but rather the goal is to determine the identity of a target (N-terminal amino acid) from the binding affinities of many binders (NAABs). In this case, one may significantly reduce the effects of calibration error by using the reference values of $k_D$ to calculate the expected photon rate E from the brightnesses of the on- and off-states, for each of the possible target identities. After having performed the measurement with all 17 binders, one is left with a vector $\vec{M}$ of the photon rates measured for each binder, and a set of vectors $\vec{E}_k$, the kth of which is the vector of photon rates that one would have expected to measure if the target were of type k. The identity of the target is then determined by minimizing the norm of $\vec{M}-\vec{E}_k$. The key difference here is that because one compares the expected photon rates to the measured photon rates, one avoids the nonlinearities inherent in calculating the measured dissociation constant from the measured photon rate.

FIG. 6 shows the full set of accuracy matrices that were determined by simulation for 100 random affinity matrices.

Single Molecule Protein Sequencing

Single molecule protein sequence is performed. In some studies a set of peptides is immobilized on a surface. In some of the studies, the peptides are attached to the surface, in a manner such that there is on average no more than one peptide per diffraction-limited spot, which results in the ability to individually resolve each peptide with the microscope. This peptide positioning is successful in tested methods of imagining single-molecule protein sequencing.

In some studies a solution that includes NAAB reagents also includes one or more degradation reagents. In these studies protein/peptide degradation occurs at essentially the same time as the luminescence measurements are made. In some studies, TIRF microscopy is used to determine NAAB binding kinetics. Some studies are performed using an electric-readout detection means to determine NAAB binding kinetics. Some studies are performed using a single-photon avalanche diode (SPAD) detection means to determine NAAB binding kinetics.

In certain of the studies, the immobilized peptide surface is imaged using total internal reflection fluorescence (TIRF) microscopy. Art-known methods are used to appropriately passivate the attachment surface to minimize nonspecific binding [see for example Tessler L A, et al., Journal of the Royal Society Interface. 2011; 8(63):1400-1408; Tessler L A. & Mitra R D. Proteomics. 2011; 11(24):4731-4735; Chandradoss S D et al., Journal of Visualized Experiments: JoVE. 2014; (86); Selvin P R. & Ha T. Cold Spring Harbor Laboratory Press; Edited by Paul R. Selvin; 2008; Joo C, et al, Trends in Biochemical Sciences. 2013; 38(1):30-37; Groll J. & Moeller M. in: Methods in Enzymology. vol. 472. Elsevier; 2010. p. 1-18; Finkelstein I J. & Greene E C. In: DNA Recombination. Springer; 2011. p. 447-461; and Pan H, et al., Physical Biology. 2015; 12(4):045006]. The limited vertical extent of the evanescent excitation field of the TIRF microscope allows differential sensitivity to fluorescent molecules that are near the microscope slide surface, which allows detection of NAABs that have bound to peptides on the surface.

Experiments are performed to deduce the identity of the N terminal amino acid of a particular peptide by measuring the binding kinetics of a set of prepared NAABs against the peptide. Methods of preparing the NAABs are described elsewhere herein. The binding of each of a set of NAAB reagents against the peptide is observed and the N-terminal amino acid of the single protein is determined and a cycle of Edman degradation is carried out, revealing the next amino acid along the chain as the new N-terminus, the new-N-terminus amino acid is identified and the process is repeated and the amino acid sequence of the protein is determined.

EQUIVALENTS

It is to be understood that the methods and compositions that have been described above are merely illustrative applications of the principles of the invention. Numerous modifications may be made by those skilled in the art without departing from the scope of the invention.

Although the invention has been described in detail for the purpose of illustration, it is understood that such detail is solely for that purpose and variations can be made by those skilled in the art without departing from the spirit and scope of the invention which is defined by the following claims.

The contents of all literature references, publications, patents, and published patent applications cited throughout this application are incorporated herein by reference in their entirety.

What is claimed is:

1. A method of identifying an N-terminal amino acid of a polypeptide, comprising:
  (a) contacting a composition comprising a polypeptide with a set of independently selected N-terminal amino acid binding (NAAB) reagents, wherein a plurality of the independently selected NAAB reagents in the set bind to the polypeptide's N-terminal amino acid and the binding of each of the independently selected NAAB reagents to the polypeptide's N-terminal amino acid produces a specific detectable signal;
  (b) determining the specific detectable signal produced by the binding of each of the plurality of the independently selected NAAB reagents to the polypeptide's N-terminal amino acid;

(c) kinetically measuring the determined specific detectable signals produced by the binding of the plurality of the independently selected NAAB reagents to the polypeptide's N-terminal amino acid;

(d) combining the kinetic measurements;

(e) determining a binding profile of the set of independently selected NAAB reagents based at least in part on the combined kinetic measurements; and (f) identifying the N-terminal amino acid in the polypeptide from the determined binding profile of the set of independently selected NAAB reagents.

2. The method of claim 1, wherein the detectable signal is a luminescent signal, and optionally is a fluorescent signal.

3. The method of claim 1, further comprising removing the N-terminal amino acid from the polypeptide to reveal a next N-terminal amino acid on the polypeptide, and repeating the steps (a)-(f) to identify the next N-terminal amino acid of the polypeptide.

4. The method of claim 3, further comprising repeating the removal of the N-terminal amino acid and steps (a)-(f) a sufficient number of times to identify a portion or all of the polypeptide's amino acid sequence.

5. The method of claim 1, wherein each of the independently selected NAAB reagents is a low affinity binding reagent for each of the polypeptide's amino acids.

6. The method of claim 1, wherein each of the independently selected NAAB reagents is a low specificity binding reagent for each of the polypeptide's amino acids.

7. The method of claim 1, wherein the kinetic measuring comprises detecting a plurality of time-averaged specific detectable signals of each of the independently selected NAAB reagents that bind the polypeptide's N-terminal amino acid.

8. The method of claim 7, wherein detecting the time-averaged signal comprises determining a length of time of the binding events of the independently selected NAAB reagents that bind the polypeptide's N-terminal amino acid.

9. The method claim 1, wherein the plurality of the independently selected NAAB reagents in the set comprises at least 5, 10, 15, 20 or more different binding reagents.

10. The method of claim 1, wherein a means of determining the specific detectable signals produced by the binding of each of the plurality of the independently selected NAAB reagents to the polypeptide's N-terminal amino acid comprises an optical detection method.

11. The method of claim 10, wherein the optical detection method comprises microscopy, and optionally the microscopy comprises total internal reflection fluorescence (TIRF) microscopy.

12. The method of claim 11, wherein the TIRF microscopy comprises kinetically measuring the determined specific detectable signals produced by the binding of the plurality of the independently selected NAAB reagents to the polypeptide's N-terminal amino acid.

13. The method of claim 1, wherein more than one detectable signal produced by the binding of each of the plurality of the independently selected NAAB reagents to the polypeptide's N-terminal amino acid are simultaneously detected.

14. The method of claim 1, wherein a high-dimensional vector of kinetically-measured affinities for the N-terminal amino acid is produced from the kinetic measurements.

15. The method of claim 1, wherein the kinetically measuring comprises measuring using a high-time resolution measuring means capable of detecting individual binding and unbinding events.

16. The method of claim 1, wherein the polypeptide is immobilized on a surface and optionally the polypeptide is immobilized in a manner to have, on average, no more than one peptide per a diffraction-limited spot.

17. The method of claim 3, wherein a means for removing the N-terminal amino acid from the polypeptide comprises a cycle of Edman degradation.

18. The method of claim 1, wherein each of the independently selected N-terminal amino acid binding reagents is derived from an independently selected aminopeptidase.

19. A method of determining an amino acid sequence of a polypeptide, comprising:
(a) contacting a composition comprising a polypeptide with a set of independently selected N-terminal amino acid binding (NAAB) reagents, wherein a plurality of the independently selected NAAB reagents in the set bind to the polypeptide's N-terminal amino acid and the binding of each of the independently selected NAAB reagents to the polypeptide's N-terminal amino acid produces a specific detectable signal;

(b) determining the specific detectable signal produced by the binding of each of the plurality of the independently selected NAAB reagents to the polypeptide's N-terminal amino acid;

(c) kinetically measuring the determined specific detectable signals produced by the binding of the plurality of the independently selected NAAB reagents to the polypeptide's N-terminal amino acid;

(d) combining the kinetic measurements;

(e) determining a binding profile of the set of independently selected NAAB reagents based at least in part on the combined kinetic measurements;

(f) identifying the N-terminal amino acid in the polypeptide from the determined binding profile of the set of independently selected NAAB reagents;

(g) removing the identified N-terminal amino acid to reveal a next N-terminal polypeptide; and (h) repeating steps (a)-(g) on the next N-terminal amino acid of the polypeptide to determine a partial or full amino acid sequence of the polypeptide.

20. A method of spectral sequencing a peptide comprising:
(a) measuring one or more of probe-target binding affinities and probe-target binding kinetics of a plurality of low-affinity, relatively non-specific N-terminal-specific amino-acid binders (NAABs) and amino acid targets;

(b) collectively determining a spectrum of affinity across the NAABs, for each of the N-terminal amino acid targets;

(c) determining the identity of the N-terminal amino acids based on the collectively determined spectrum of affinity across the NAABs; and (d) sequencing a peptide based on the determined identities of the N-termination amino acids.

* * * * *